(12) United States Patent
Tsukada et al.

(10) Patent No.: US 10,881,295 B2
(45) Date of Patent: Jan. 5, 2021

(54) OPHTHALMIC SYSTEM, OPHTHALMIC INFORMATION PROCESSING APPARATUS, AND OPHTHALMIC INFORMATION PROCESSING METHOD

(71) Applicant: TOPCON CORPORATION, Tokyo (JP)

(72) Inventors: Hisashi Tsukada, Hachioji (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 249 days.

(21) Appl. No.: 16/046,244

(22) Filed: Jul. 26, 2018

(65) Prior Publication Data
US 2019/0029514 A1    Jan. 31, 2019

(30) Foreign Application Priority Data
Jul. 26, 2017   (JP) ................................. 2017-144590

(51) Int. Cl.
*A61B 3/135* (2006.01)
*A61B 3/00* (2006.01)
*A61B 3/14* (2006.01)

(52) U.S. Cl.
CPC ............ *A61B 3/135* (2013.01); *A61B 3/0025* (2013.01); *A61B 3/0058* (2013.01); *A61B 3/14* (2013.01)

(58) Field of Classification Search
CPC ..... A61B 3/135; A61B 3/0025; A61B 3/0058; A61B 3/14
(Continued)

(56) References Cited

U.S. PATENT DOCUMENTS

2003/0063258 A1*  4/2003  Torii ...................... A61B 3/117
                                                                351/214
2008/0151187 A1    6/2008  Tsukada et al.
(Continued)

FOREIGN PATENT DOCUMENTS

EP          1935329 A1      6/2008
JP        2000-116732 A     4/2000
(Continued)

OTHER PUBLICATIONS

Extended European Search Report dated Dec. 12, 2018 in European Application No. 18185205.4-1124.

*Primary Examiner* — Thomas K Pham
*Assistant Examiner* — Mitchell T Oestreich
(74) *Attorney, Agent, or Firm* — Xsensus LLP

(57) ABSTRACT

An ophthalmic system of an embodiment includes a slit lamp microscope and an information processing apparatus. The slit lamp microscope includes an image acquisition device that acquires a three dimensional image by photographing a subject's eye, and a first communication device that transmits the three dimensional image to the information processing apparatus. The information processing apparatus includes a second communication device that receives the three dimensional image transmitted by the first communication device, a display controller that displays a first image based on the three dimensional image on a display device, a partial region designation processor that designates a partial region of the first image, and a rendering processor that renders the three dimensional image based on the partial region to construct a second image. The display controller displays the second image on the display device.

15 Claims, 9 Drawing Sheets

(58) Field of Classification Search
USPC .......................................................... 351/206
See application file for complete search history.

(56) References Cited

U.S. PATENT DOCUMENTS

2015/0085252 A1  3/2015  Fujimura et al.
2016/0345822 A1  12/2016  Fujimura et al.

FOREIGN PATENT DOCUMENTS

| | | |
|---|---|---|
| JP | 2007-029460 A | 2/2007 |
| JP | 2013-248376 A | 12/2013 |
| JP | 2016-159073 A | 9/2016 |
| JP | 2016-179004 A | 10/2016 |

* cited by examiner

OPHTHALMIC SYSTEM, OPHTHALMIC INFORMATION PROCESSING APPARATUS, AND OPHTHALMIC INFORMATION PROCESSING METHOD

CROSS-REFERENCE TO RELATED APPLICATIONS

This application is based upon and claims the benefit of priority from Japanese Patent Application No. 2017-144590, filed Jul. 26, 2017; the entire contents of which are incorporated herein by reference.

FIELD

Embodiments described herein relate to an ophthalmic system, an ophthalmic information processing apparatus, and an ophthalmic information processing method.

BACKGROUND

Diagnostic imaging serves an important role in the field of ophthalmology. Various kinds of ophthalmic imaging apparatuses are utilized for diagnostic imaging. Examples of ophthalmic imaging apparatuses include a slit lamp microscope, a fundus camera, a scanning laser ophthalmoscope (SLO), an optical coherence tomography (OCT), and the like. In addition, various kinds of ophthalmic imaging apparatuses such as a refractometer, a keratometer, a tonometer, a specular microscope, a wave front analyzer, and a microperimeter are equipped with the function of imaging anterior eye segment and/or the function of imaging eye fundus.

A slit lamp microscope is one of the most widely and frequently utilized apparatuses among various kinds of ophthalmic apparatuses. A slit lamp microscope is an ophthalmic apparatus for illuminating a subject's eye with slit light and observing and/or photographing the illuminated cross section from an oblique position with a microscope. A slit lamp microscope is utilized in general for diagnosis of the anterior eye segment such as the cornea or the crystalline lens. For example, a doctor observes an entire diagnostic site while moving the focal position and the area illuminated by the slit light to determine the presence or absence of abnormality.

Meanwhile, research and development on telemedicine (or remote medicine) technology has been developing with the advancement of information communication technology in recent years. Telemedicine is an act of performing medical care on a patient located in a remote place by using information technology such as the Internet.

Examples of documents related to the background art as described above include Japanese Unexamined Patent Application Publication No. 2016-159073, Japanese Unexamined Patent Application Publication No. 2016-179004, and Japanese Unexamined Patent Application Publication No. 2000-116732.

For example, Japanese Unexamined Patent Application Publication No. 2000-116732 discloses a technique for operating a medical apparatus from a distant location. However, the remote operation disclosed in Japanese Unexamined Patent Application Publication No. 2000-116732 has a restriction that a doctor who is present in a distant place is required to perform operations of the medical apparatus in real time.

In addition, various kinds of delicate manipulations such as movement of the illumination system, movement of the imaging system, setting of the slit width, and setting of the focal position are necessary to operate a slit lamp microscope. Performing these operations from a distant location is not easy even for an expert.

As such, with the conventional telemedicine technology, it has been impossible to effectively utilize the slit lamp microscope which is most widely and frequently utilized for diagnostic imaging in the field of ophthalmology.

DETAILED DESCRIPTION

Figure 1:
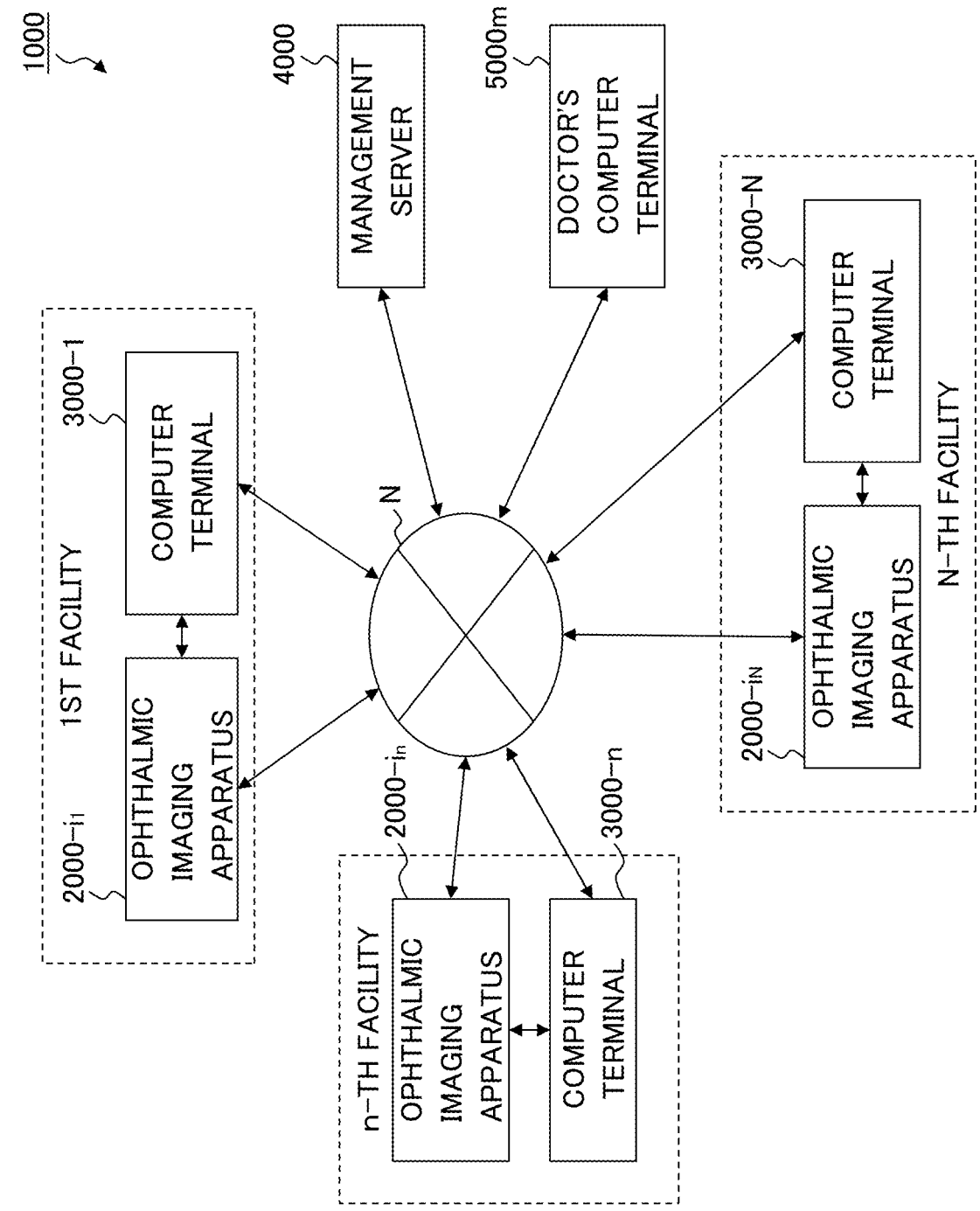
FIG. 1 is a schematic diagram illustrating an example of the configuration of an ophthalmic system according to an exemplary embodiment.

A purpose of the exemplary embodiment described below is to provide an ophthalmic telemedicine technology capable of effectively utilizing a slit lamp microscope.

The first aspect of the exemplary embodiment is an ophthalmic system that includes a slit lamp microscope and an information processing apparatus. The slit lamp microscope and the information processing apparatus are connected to each other via a communication path. The slit lamp microscope includes an image acquisition device that acquires a three dimensional image by photographing a subject's eye, and a first communication device that transmits the three dimensional image to the information processing apparatus. The information processing apparatus includes a second communication device that receives the three dimensional image transmitted by the first communication device, a display controller that displays a first image based on the three dimensional image on a display device, a partial region designation processor that designates a partial region of the first image, and a rendering processor that renders the three dimensional image based on the partial region to construct a second image. The display controller displays the second image on the display device.

The second aspect of the exemplary embodiment is the ophthalmic system of the first aspect, wherein the information processing apparatus further includes an operation device, and the partial region designation processor designates the partial region based on a signal output from the operation device.

The third aspect of the exemplary embodiment is the ophthalmic system of the first aspect, wherein the partial region designation processor analyzes at least one of the three dimensional image and the first image to designate the partial region.

The fourth aspect of the exemplary embodiment is the ophthalmic system of any of the first to third aspects, wherein the image acquisition device includes an illumination system that illuminates the subject's eye with slit light, an imaging system that guides returning light of the slit light from the subject's eye to an imaging device, and a movement device that moves the illumination system and the imaging system. In addition, the ophthalmic system further includes a three dimensional image construction processor that constructs a three dimensional image based on a plurality of cross sectional images acquired by the imaging device in parallel with movement of the illumination system and the imaging system.

The fifth aspect of the exemplary embodiment is the ophthalmic system of the fourth aspect, wherein the image acquisition device further includes a focal position changer for changing at least one of a focal position of the illumination system and a focal position of the imaging system, and the three dimensional image construction processor constructs a three dimensional image based on a plurality of cross sectional images acquired by the imaging device in parallel with both movement of at least one of the illumination system and the imaging system and change in at least one of the focal position of the illumination system and the focal position of the imaging system.

The sixth aspect of the exemplary embodiment is the ophthalmic system of the fifth aspect, further including an operation mode designation device for designating an operation mode of the slit lamp microscope. In addition, the slit lamp microscope further includes a controller that controls the illumination system, the imaging system, the movement device, and the focal position changer in an interlocking manner to make the imaging device acquire the plurality of cross sectional images when a three dimensional imaging mode has been designated using the operation mode designation device.

The seventh aspect of the exemplary embodiment is the ophthalmic system of any of the first to sixth aspects, wherein the display controller displays position information indicating a position of the second image on the display device.

The eighth aspect of the exemplary embodiment is the ophthalmic system of any of the first to seventh aspects, wherein the slit lamp microscope further includes a reception part that receives subject information, and the first communication device transmits the subject information together with the three dimensional image.

The ninth aspect of the exemplary embodiment is the ophthalmic system of any of the first to eighth aspects, wherein the image acquisition device further acquires a front image by photographing the subject's eye, and the first communication device transmits the front image together with the three dimensional image.

The tenth aspect of the exemplary embodiment is an ophthalmic information processing apparatus that includes a communication device that receives a three dimensional image acquired by photographing a subject's eye with a slit lamp microscope via a communication path, a display controller that displays a first image based on the three dimensional image on a display device, a partial region designation processor that designates a partial region of the first image, and a rendering processor that renders the three dimensional image based on the partial region to construct a second image. The display controller displays the second image on the display device.

The eleventh aspect of the exemplary embodiment is a method of processing ophthalmic information executed by an ophthalmic system that includes a slit lamp microscope and an information processing apparatus that are connected to each other via a communication path. The method includes the following steps: acquiring a three dimensional image by photographing a subject' eye with the slit lamp microscope; transmitting the three dimensional image from the slit lamp microscope to the information processing apparatus; receiving the three dimensional image with the information processing apparatus; displaying a first image based on the three dimensional image on a display device; designating a partial region of the first image; constructing a second image by rendering the three dimensional image based on the partial region; and displaying the second image on the display device.

The twelfth aspect of the exemplary embodiment is a method of processing ophthalmic information executed by an information processing apparatus that is connected to a slit lamp microscope via a communication path. The method includes the following steps: receiving a three dimensional image acquired by photographing a subject's eye with the slit lamp microscope via a communication path; displaying a first image based on the three dimensional image on a display device; designating a partial region of the first image; constructing a second image by rendering the three dimensional image based on the partial region; and displaying the second image on the display device.

An ophthalmic system, an ophthalmic information processing apparatus, and an ophthalmic information processing method according to exemplary embodiments will be described in detail with referring to the drawings. It should be noted that any of the matters and items disclosed in the documents cited in the present specification and any known techniques and technologies can be incorporated into the embodiments.

The ophthalmic system of the embodiment can be utilized for telemedicine using an ophthalmic imaging apparatus installed in any kind of facility and/or a portable ophthalmic imaging apparatus. Telemedicine described in the embodiment involves at least a doctor who performs interpretation of a medical image acquired by an ophthalmic imaging apparatus. Here, the doctor performs the interpretation at a location distant from the facility where the ophthalmic imaging apparatus is installed. Further, telemedicine according to the embodiment may also involve a person (an assistant) who assists the examination at the facility where the ophthalmic imaging apparatus is installed.

Examples of the facility in which the ophthalmic imaging apparatus is installed include a health facility, an optician's store, a health check and screening venue, a patient's home, a welfare facility, a public facility, an examination vehicle, and the like.

The ophthalmic imaging apparatus may be any kind of apparatus utilized for the imaging of eyes and includes a slit lamp microscope. Also, any of the plurality of ophthalmic imaging apparatuses included in the ophthalmic system may be any kind of modalities other than slit lamp microscopes. For example, the modalities may include fundus cameras, SLOs, or OCTs. Furthermore, the ophthalmic imaging apparatus may be provided with application software for analyzing measurement data, captured images, or the like.

The ophthalmic system of the embodiment may further include an ophthalmic measurement apparatus for measuring the characteristics of eyes. Examples of the ophthalmic measurement apparatus include a visual acuity test apparatus (visual target presenting apparatus, phoropter, etc.), an eye refraction test apparatus (refractometer, keratometer, etc.), a tonometer, a specular microscope, a wave front analyzer, a perimeter, a micro perimeter, and the like.

<Ophthalmic System>

An example of the configuration of the ophthalmic system according to the embodiment will be described. The ophthalmic system 1000 illustrated in FIG. 1 as an example is configured by using a communication path (a communication line) N that connects N facilities (first to N-th facilities) at which ophthalmic imaging is performed, the management server 4000, and the doctor's computer terminal 5000m.

Each of the facilities (n-th facility: where n=1 to N, N is any positive integer) is provided with the ophthalmic imaging apparatus 2000-$i_n$ (where $i_n$=1 to $K_n$, $K_n$ is any positive integer). In other words, one or more ophthalmic imaging apparatuses 2000-$i_n$ are installed in each of the facilities (n-th facility). The ophthalmic imaging apparatus 2000-$i_n$ constitutes a part of the ophthalmic system 1000. Incidentally, the ophthalmic system 1000 may include an examination apparatus that is capable of performing examination other than ophthalmic examination.

The ophthalmic imaging apparatus 2000-$i_n$ of the present example has the function of an "imaging apparatus" that performs imaging of eyes, and the function of a "computer" that performs various kinds of data processing and communicates with external devices. For another example, an imaging apparatus and a computer may be provided separately from each other. If this is the case, the imaging apparatus and the computer may communicate with each other. There may be any number of imaging apparatuses and any number of computers. For example, a single computer and a plurality of imaging apparatuses can be provided.

Each of the facilities (n-th facility) is provided with an information processing apparatus used by an assistant or a subject (i.e., the computer terminal 3000-n). The computer terminal 3000-n is a computer for use in the corresponding facility. The computer terminal 3000-n may be, for example, a mobile computer terminal such as a tablet computer terminal or a smartphone, or a server installed in the corresponding facility. The computer terminal 3000-n may also include a wearable device such as a wireless earphone. Note that the computer terminal 3000-n is only required to be a computer capable of realizing its functions in the corresponding facility. The computer terminal 3000-n may be, for example, a computer placed outside the corresponding facility such as a cloud server.

The ophthalmic imaging apparatus 2000-$i_n$ and the computer terminal 3000-n may communicate with each other through a network such as a network built in the n-th facility (e.g., in-house LAN), a wide area network (e.g., the Internet), or near-field communication technology.

The ophthalmic imaging apparatus 2000-$i_n$ may have the function as a server. If this is the case, the ophthalmic imaging apparatus 2000-$i_n$ and the computer terminal 3000-n may communicate directly with each other. This makes it possible for the management server 4000 and the computer terminal 3000-n to communicate with each other via the ophthalmic imaging apparatus 2000-$i_n$. Therefore, the function to perform communication between the computer terminal 3000-n and the management server 4000 becomes unnecessary.

The management server 4000 is installed in the management center, for example. The management server 4000 can communicate with the doctor's computer terminal 5000m (where m=1 to M, M is any positive integer) via a network. The network is, for example, a LAN or a wide area network. Further, the management server 4000 can communicate with at least one of the ophthalmic imaging apparatuses 2000-$i_n$ installed in the first to the n-th facilities via a wide area network.

The management server 4000 has, for example, the function of relaying communication between the ophthalmic imaging apparatus 2000-$i_n$ and the doctor's computer terminal 5000m, and the function of recording the contents of the communication. In addition, the management server 4000 may have a data processing function. For example, the management server 4000 may include a three dimensional image construction processor that executes processing of constructing a three dimensional image from a plurality of cross sectional images of the subject's eye. The three dimensional image construction processor includes a processor, a computer program, etc.

The doctor's computer terminal 5000m includes a computer used for interpretation of images of the subject's eye acquired by the ophthalmic imaging apparatus 2000-$i_n$.

The "processor" as used in the present embodiment is a circuit such as a central processing unit (CPU), a graphics processing unit (GPU), an application specific integrated circuit (ASIC), and a programmable logic device (PLD). Examples of the PLD include a simple programmable logic device (SPLD), a complex programmable logic device (CPLD), and a field programmable gate array (FPGA). For example, the processor loads a program or data stored in a memory circuit or a storage, and executes the program, thereby implementing the functions according to the embodiment.

<Configuration of the Ophthalmic Imaging Apparatus>

A description is given of an example of the configuration of the ophthalmic imaging apparatus 2000-$i_n$. Although the ophthalmic imaging apparatus 2000-$i_n$ may be any modality as described above, a slit lamp microscope is employed in the present embodiment.

Here, the directions are defined. The front direction (or the depth direction) is defined as the direction towards the subject from the lens positioned closest to the subject (objective lens) in the optical system of the slit lamp microscope. The back direction is defined as the opposite direction of the front direction. The lateral direction (or the left and right direction) is defined as the horizontal direction orthogonal to the front direction. Further, the vertical direction (or the up and down direction) is defined as the direction orthogonal to both the front-back direction and the lateral direction.

Figure 2:
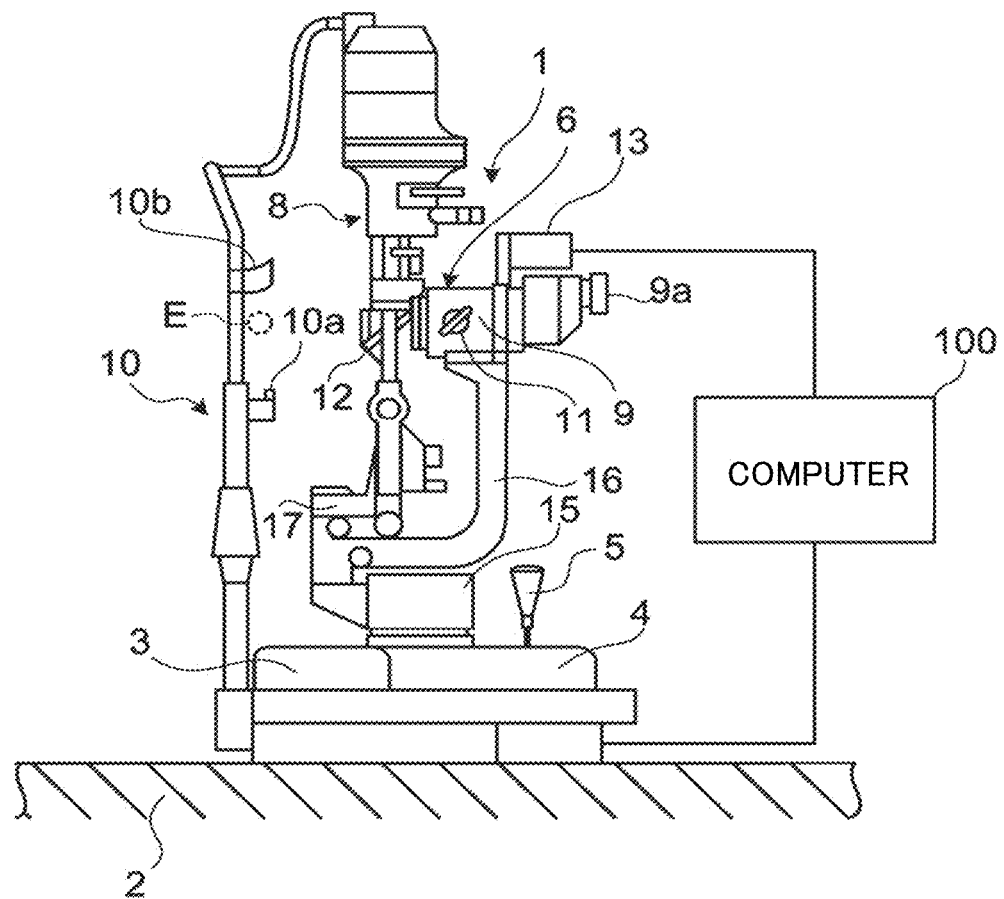
FIG. 2 is a schematic diagram illustrating an example of the configuration of the ophthalmic system according to the exemplary embodiment.

FIG. 2 shows an example of the exterior configuration of the slit lamp microscope. The computer 100 is connected to the slit lamp microscope 1. The computer 100 executes various kinds of control processing and arithmetic processing. The configuration in which a computer like the computer 100 is provided in the main body of the microscope (housing thereof that stores optical systems etc.) can also be employed in place of providing the computer 100 separately from the main body of the microscope. At least part of the computer 100 and at least part of the aforementioned computer terminal 3000-n may be common.

The slit lamp microscope 1 is placed on the table 2. The base 4 is configured to be movable in the horizontal direction via the movement mechanism part 3. The base 4 is moved by tilting the operation handle 5.

The support portion 15 is provided on the upper surface of the base 4. The support portion 15 is configured to support the observation-photographing system 6 and the illumination system 8. The support arm 16 that supports the observation-photographing system 6 is attached to the support portion 15. The support arm 16 is rotatable (i.e., moving in a circular path) in the lateral direction. The support arm 17 that supports the illumination system 8 is attached to the upper portion of the support arm 16. The support arm 17 is rotatable in the lateral direction. The support arms 16 and 17 are independently rotatable in a coaxial manner with each other.

The observation-photographing system 6 is moved by the rotation of the support arm 16. The illumination system 8 is moved by the rotation of the support arm 17. Each of the support arms 16 and 17 is rotated by an electrical mechanism. The movement mechanism part 3 is provided with a mechanism for rotating the support arm 16 and a mechanism for rotating the support arm 17. The movement of the observation-photographing system 6 may be performed by manual rotation of the support arm 16. Likewise, the movement of the illumination system 8 may be performed by manual rotation of the support arm 17.

The illumination system 8 illuminates the subject's eye E with illumination light. As described above, the illumination system 8 can be rotated in the lateral direction. Further, the illumination system 8 may be rotatable in the vertical direction. In other words, the elevation angle and the depression angle of the illumination system 8 may be changeable. By such swinging motions of the illumination system 8, the projection direction of the illumination light with respect to the subject's eye E can be changed.

The observation-photographing system 6 includes a pair of left and right optical systems. Each of the left and right optical systems is configured to guide returning light of the illumination light projected onto the subject's eye E. The left and right optical systems are stored in the body tube (or, lens tube, lens barrel, etc.) 9. The terminal end of the body tube 9 is the eyepiece portion 9a. The examiner observes the subject's eye E by looking into the eyepiece portion 9a. As described above, the body tube 9 can be rotated in the lateral direction by the rotation of the support arm 16. Further, the observation-photographing system 6 may be configured to rotatable in the vertical direction. In other words, the elevation angle and the depression angle of the observation-photographing system 6 may be changeable. By such swinging motions of the observation-photographing system 6, the direction of photographing the subject's eye E can be changed.

The chin rest base 10 is disposed at a position facing the body tube 9. The chin rest base 10 is provided with the chin rest 10a and the forehead rest 10b for stably positioning the face of the subject.

The magnification operation knob 11 is disposed on the side surface of the body tube 9. The magnification operation knob 11 is operated to change the magnification. Furthermore, the imaging device 13 that captures an image of the subject's eye E is connected to the body tube 9. The imaging device 13 includes an image sensor. The image sensor is a photoelectric conversion element that detects light and outputs the image signal GS (electric signal). The image signal GS is input to the computer 100. The image sensor may be a charge-coupled device (CCD) image sensor or a complementary metal oxide semiconductor (CMOS) image sensor. The mirror 12 is disposed at the lower position of the illumination system 8. The mirror 12 redirects the illumination light beam output from the illumination system 8 toward the subject's eye E.

<Configuration of the Optical Systems>

Figure 3:
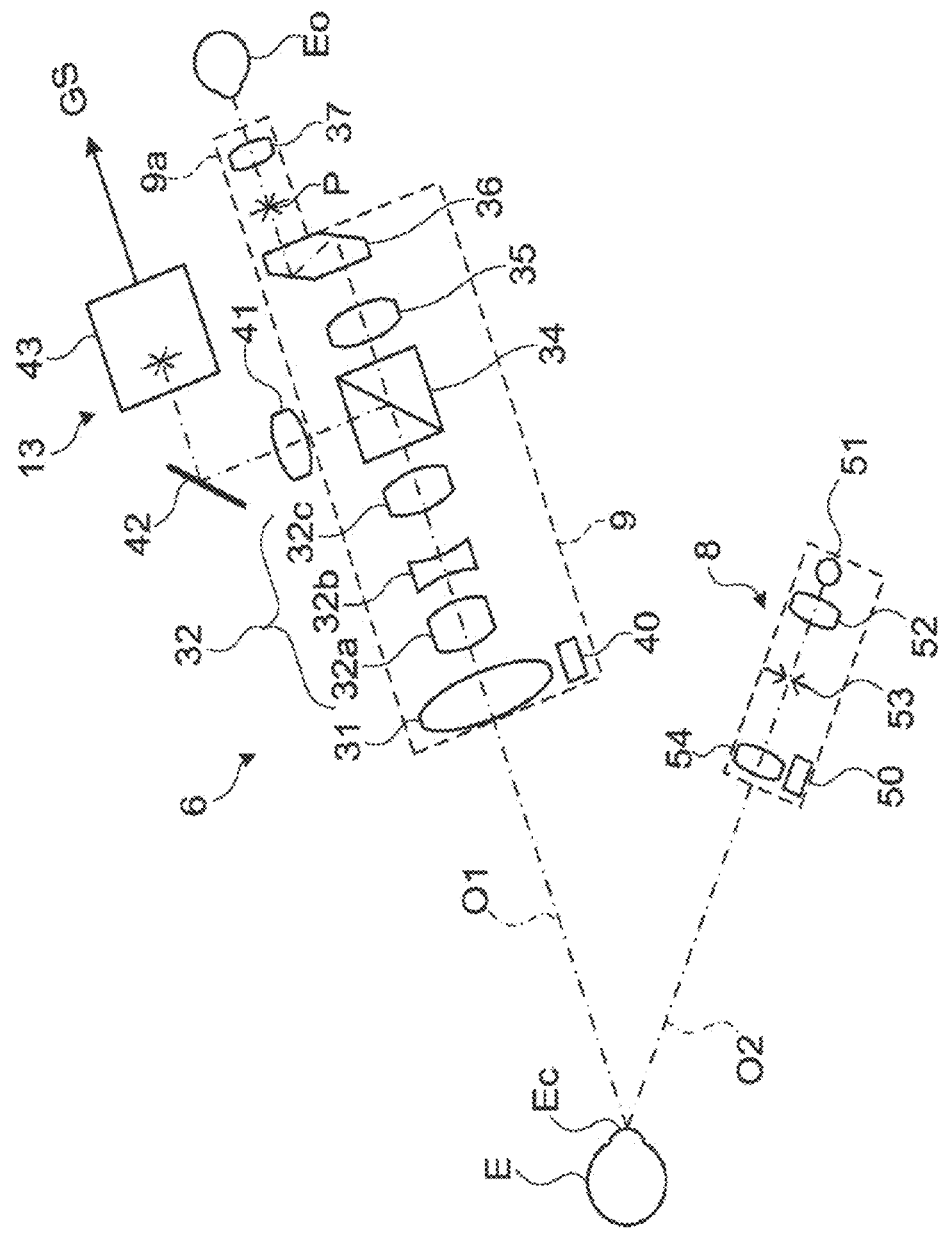
FIG. 3 is a schematic diagram illustrating an example of the configuration of the ophthalmic system according to the exemplary embodiment.

FIG. 3 shows an example of the configuration of the optical systems of the slit lamp microscope 1. As described above, the slit lamp microscope 1 includes the observation-photographing system 6 and the illumination system 8.

<Observation-Photographing System 6>

The observation-photographing system 6 includes a pair of left and right optical systems. The left and right optical systems have almost the same configuration. The examiner can observe the subject's eye E with both eyes through the left and right optical systems. FIG. 3 shows only one of the left and right optical systems of the observation-photographing system 6. The observation-photographing system 6 may include only one of the left and right optical systems. The reference symbol O1 indicates the optical axis of the observation-photographing system 6.

Each of the left and right optical systems of the observation-photographing system 6 includes the objective lens 31, the variable magnification optical system (or zooming optical system) 32, the beam splitter 34, the imaging lens 35, the prism 36, and the eyepiece 37. Here, the beam splitter 34 is provided in one or both of the left and right optical systems. The eyepiece 37 is provided inside the eyepiece portion 9a. The reference symbol P indicates the imaging position of the light guided to the eyepiece 37. The reference symbol Ec indicates the cornea of the subject's eye E. The reference symbol Eo indicates the examiner's eye.

The variable magnification optical system 32 includes a plurality of (e.g., three) variable magnification lenses 32a, 32b, and 32c. In the present embodiment, a plurality of variable magnification lens groups is provided. The plurality of variable magnification lens groups are selectively inserted into the optical path of the observation-photographing system 6. The plurality of variable magnification lens groups respectively correspond to magnifications differing from one another. One of the plurality of variable magnification lens groups selectively disposed in the optical path of the observation-photographing system 6 is used as the variable magnification optical system 32. The selective insertion of the plurality of variable magnification lens groups performed in this way makes it possible to change the magnification (angle of view) of the photographed image and the observation image of the subject's eye E. The change in the magnification, that is, the selection of the variable magnification lens group to be disposed in the optical path of the observation-photographing system 6, is performed by the operation of the magnification operation knob 11. Further, the configuration may be employed in which the magnification is changed electrically by using a switch (not shown) or the like.

The beam splitter 34 splits the optical path of the light traveling along the optical axis O1 into an optical path located on the extension of the optical axis O1 and an optical path orthogonal to the optical axis O1. The light incident on the optical path located on the extension of the optical axis O1 is guided to the examiner's eye Eo via the imaging lens 35, the prism 36, and the eyepiece 37. The prism 36 translates the traveling direction of the light upward.

On the other hand, the light incident on the optical path orthogonal to the optical axis O1 is guided to the image sensor 43 of the imaging device 13 via the condenser lens 41 and the mirror 42. In other words, the observation-photographing system 6 guides the returning light from the subject's eye E to the imaging device 13. The image sensor 43 detects the returning light and generates the image signal GS.

The observation-photographing system 6 includes the focus mechanism 40 for changing the focal position of the observation-photographing system 6. The focus mechanism 40 moves the objective lens 31 along the optical axis O1. For example, the focus mechanism 40 includes a holding member that holds the objective lens 31, a sliding mechanism that moves the holding member in the direction along the optical axis O1, an actuator that generates driving force, a members that transmits the driving force to the sliding mechanism.

The movement of the objective lens 31 is carried out automatically and/or manually. In the case where automatic movement of the objective lens 31 is employed, for example, the computer 100 can determine the focal position based on the returning light from the subject's eye E using a known focus adjustment method (e.g., a phase difference detection method, or a contrast detection method). Further, the computer 100 can control the actuator to move the objective lens 31 along the optical axis O1 to the focal position determined. On the other hand, in the case where manual movement of the objective lens 31 is employed, the actuator moves the objective lens 31 along the optical axis O1 according to an operation performed by the user.

The observation-photographing system 6 may include a first focusing lens that is disposed at a position on the optical axis O1 between the objective lens 31 and the image sensor 43. When the first focusing lens is included, the focus mechanism 40 changes the focal position of the observation-photographing system 6 by moving the first focusing lens along the optical axis O1. For example, the focus mechanism 40 includes a holding member that holds the first focusing lens, a sliding mechanism that moves the holding member in the direction along the optical axis O1, an actuator that generates a driving force, and a member that transmits the driving force to the sliding mechanism. As in the case where the objective lens 31 is moved, the movement of the first focusing lens with the focus mechanism 40 is carried out automatically or manually.

Further, the entire (or, part of the) observation-photographing system 6 may be configured to be movable along the optical axis O1. If this is the case, the focus mechanism 40 changes the focal position of the observation-photographing system 6 by moving the entire (or, part of the) observation-photographing system 6 along the optical axis O1. For example, the focus mechanism 40 includes a movable stage on which the entire (or, part of the) observation-photographing system 6 is placed, a sliding mechanism that moves the movable stage in the direction along the optical axis O1, an actuator that generates a driving force, and a member that transmits the driving force to the sliding mechanism. As in the case where the objective lens 31 is moved, the movement of the observation-photographing system 6 with the focus mechanism 40 is carried out automatically or manually.

<Illumination System 8>

The illumination system 8 includes the illumination light source 51, the condenser lens 52, the slit forming part 53, and the objective lens 54. The reference symbol O2 indicates the optical axis of the illumination system 8.

The illumination light source 51 outputs illumination light. The illumination system 8 may include a plurality of light sources. For example, the illumination light source 51 may include both a light source that outputs steady light or continuous light and a light source that outputs flash light. Examples of the light source that outputs steady light or continuous light include a halogen lamp and a light emitting diode (LED). Examples of the light source that outputs flash light include a xenon lamp and an LED. The illumination light source 51 may include a light source for the observation of anterior segment and another light source for the observation of posterior eye segment. For example, the illumination light source 51 includes a visible light source that outputs visible light. The illumination light source 51 may also include an infrared light source that outputs infrared light. The center wavelength of the infrared light is, for example, a value between 800 nm and 1000 nm.

The slit forming part 53 is used to generate slit light. The slit forming part 53 has a pair of slit blades. The width of the slit light to be generated can be changed by changing the interval between the slit blades. The interval between the slit blades are called slit width.

The illumination system 8 includes the focus mechanism 50 for changing the focal position of the slit light. The focus mechanism 50 moves the objective lens 54 along the optical axis O2. For example, the focus mechanism 50 includes a holding member that holds the objective lens 54, a sliding mechanism that moves the holding member in the direction along the optical axis O1, an actuator that generates a driving force, and a member that transmits the driving force to the sliding mechanism.

The movement of the objective lens 54 is carried out automatically and/or manually. In the case where the automatic movement of the objective lens 54 is employed, for example, the computer 100 can determine the focal position by analyzing an image that depicts the image corresponding to the returning light from the subject's eye E. Further, the computer 100 can control the actuator to move the objective lens 54 along the optical axis O2 to the focal position determined. On the other hand, in the case where manual movement of the objective lens 54 is employed, the actuator moves the objective lens 54 along the optical axis O2 according to an operation performed by the user.

The illumination system 8 may include a second focusing lens that is disposed at a position on the optical axis O2 between the objective lens 54 and the slit forming part 53. When the second focusing lens is included, the focus mechanism 50 changes the focal position of the slit light by moving the second focusing lens along the optical axis O2. For example, the focus mechanism 50 includes a holding member that holds the second focusing lens, a sliding mechanism that moves the holding member in the direction along the optical axis O2, an actuator that generates a driving force, and a member that transmits the driving force to the sliding mechanism. As in the case where the objective lens 54 is moved, the movement of the second focusing lens with the focus mechanism 50 is carried out automatically or manually.

Further, the entire illumination system 8 (or part of the illumination system 8) may be movable along the optical axis O2. If this is the case, the focus mechanism 50 changes the focal position of the slit light by moving the entire (or part of the) illumination system 8 along the optical axis O2. For example, the focus mechanism 50 includes a movable stage on which the illumination system 8 is placed, a sliding mechanism that moves the movable stage in the direction along the optical axis O2, an actuator that generates a driving force, and a member that transmits the driving force to the sliding mechanism. As in the case where the objective lens 54 is moved, the movement of the illumination system 8 with the focus mechanism 50 is carried out automatically or manually.

Although not shown in FIG. 3, the mirror 12 is disposed in the optical axis O2. The mirror 12 redirects the illumination light beam output from the illumination system 8 toward the subject's eye E. Typically, the illumination system 8 and the mirror 12 are capable of rotating together.

The slit lamp microscope 1 can acquire a plurality of images by photographing the subject's eye E multiple times in parallel with performing the changes in the illumination angle and the photographing angle with respect to the subject's eye E. In other words, the slit lamp microscope 1 can acquire a plurality of cross sectional images of the subject's eye E by photographing the subject's eye E multiple times in parallel with performing the rotation of the illumination system 8 and the rotation of the observation-photographing system 6.

To each of the plurality of cross sectional images acquired through such control, position information indicating the corresponding acquisition position (e.g., corresponding cross sectional position) is assigned. For example, the position information may include any one or more of the followings: the rotational position of the illumination system 8; the rotational position of the observation-photographing system 6; the position of the cross section in the front image of the subject's eye E; and information created based on any of these.

The rotational position of the illumination system 8 and/or the rotational position of the observation-photographing system 6 can be detected, for example, with a rotational position detector including an encoder or the like. Alternatively, the rotational position of the illumination system 8 and/or the rotational position of the observation-photographing system 6 can be recognized by the computer 100 that controls the rotations. Further, the position of the cross section in the front image of the subject's eye E can be determined based on, for example, another front image of the subject's eye E and the result of detection obtained by the rotational position detector. A three dimensional image of the subject's eye E can be constructed from the plurality of cross sectional images and the plurality of pieces of position information respectively assigned to the cross sectional images. Details of this processing will be described later.

It is to be noted that the plurality of times of photography of the subject's eye E carried out in parallel with performing the changes in the illumination angle and the photographing angle may be performed while the illumination angle and/or the photographing angle are/is changing, as well as while the change(s) in the illumination angle and/or the photographing angle are/is being stopped. Further, the change in the illumination angle may be in a continuous or intermittent manner. The change in the photographing angle may also be in a continuous or intermittent manner.

The slit lamp microscope 1 can acquire a plurality of images by photographing the subject's eye E multiple times in parallel with performing the change in the focal position with respect to the subject's eye E. More specifically, the slit lamp microscope 1 can acquire a plurality of cross sectional images of the subject's eye E by photographing the subject's eye E multiple times in parallel with performing at least one of the change in the focal position of the observation-photographing system 6 and the change in the focal position of the illumination system 8.

To each of the plurality of cross sectional images acquired through such control, position information indicating the corresponding acquisition position (e.g., corresponding focal position) is assigned. The position information may include any one or more of the followings: the contents of control for the focus mechanism 40; the contents of control for the focus mechanism 50; the position of the object (e.g., the objective lens 31, the first focusing lens, or the observation-photographing system 6) to be moved by the focus mechanism 40; the position of the object (e.g., the objective lens 54, the second focusing lens, or the illumination system 8) to be moved by the focus mechanism 50; and information created based on any of these.

The control contents for the focus mechanism 40 or 50 can be recognized, for example, by the computer 100 that controls the focus mechanisms 40 or 50. The position of the object to be moved by the focus mechanism 40 or 50 can be detected, for example, by a position detector including an encoder or the like. A three dimensional image of the subject's eye E can be constructed from the plurality of cross sectional images and the plurality of pieces of position information respectively assigned to the cross sectional images. Details of this processing will be described later.

It is to be noted that the plurality of times of photography of the subject's eye E carried out in parallel with performing the change in the focal position may be performed while the focal position is changing, as well as while the change in the focal position is being stopped. Further, the change in the focal position may be in a continuous or intermittent manner.

The two kinds of controls described above can be combined. More specifically, the slit lamp microscope 1 can acquire a plurality of cross sectional images by photographing the subject's eye E multiple times in parallel with performing the changes in the illumination angle, the photographing angle, and the focal position. To each of the plurality of cross sectional images acquired through the combined control, position information indicating the corresponding acquisition positions (cross sectional position and focal position) is assigned.

<Configuration of Control System>

Figure 4:
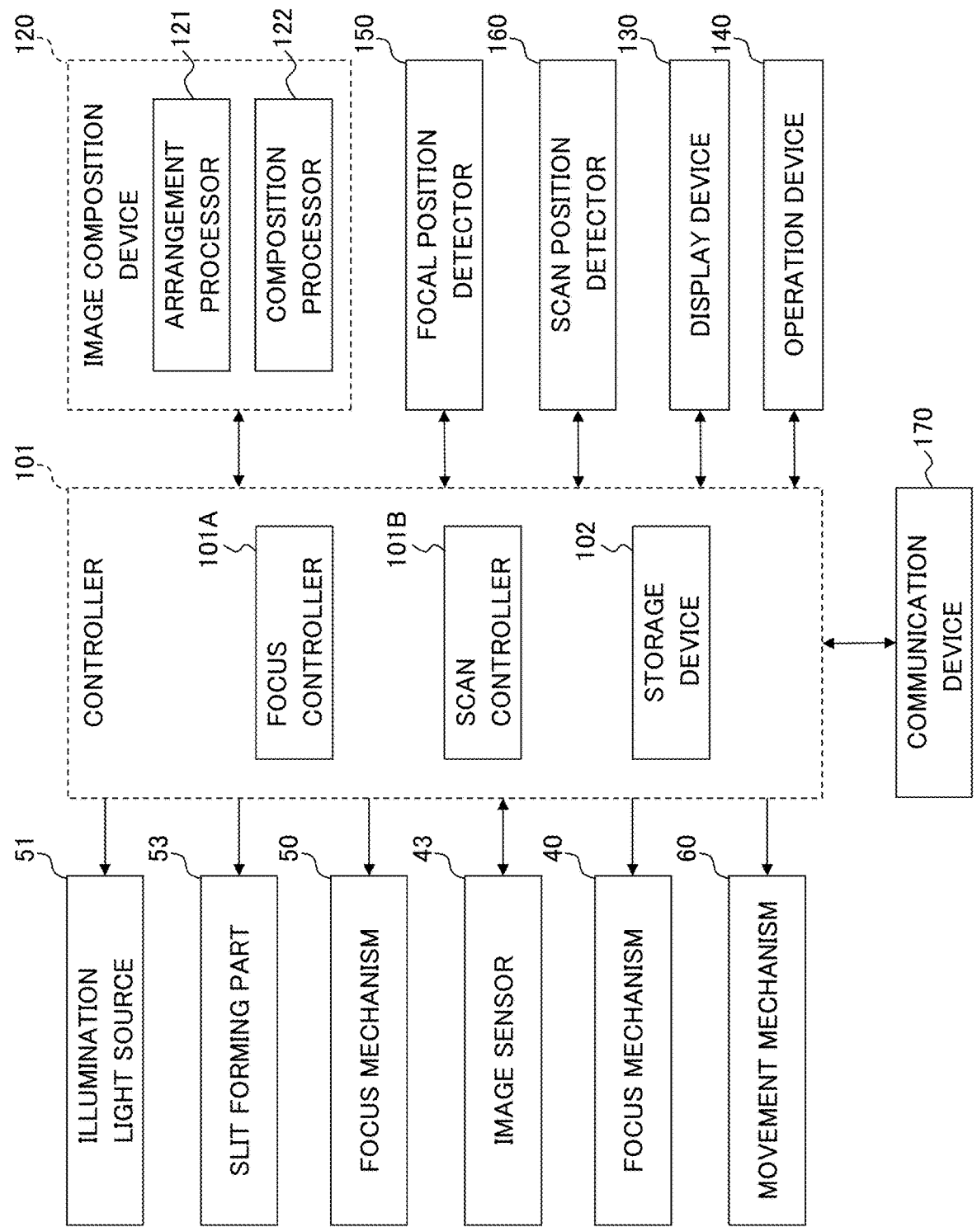
FIG. 4 is a schematic diagram illustrating an example of the configuration of the ophthalmic system according to the exemplary embodiment.
Figure 5:
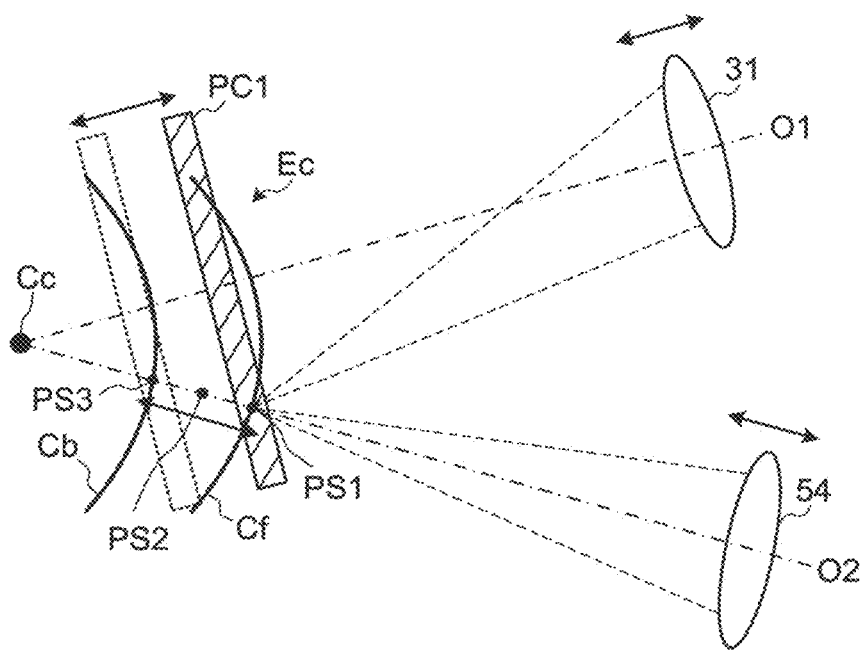
FIG. 5 is a schematic diagram for describing an example of the operation of the ophthalmic system according to the exemplary embodiment.
Figure 6:
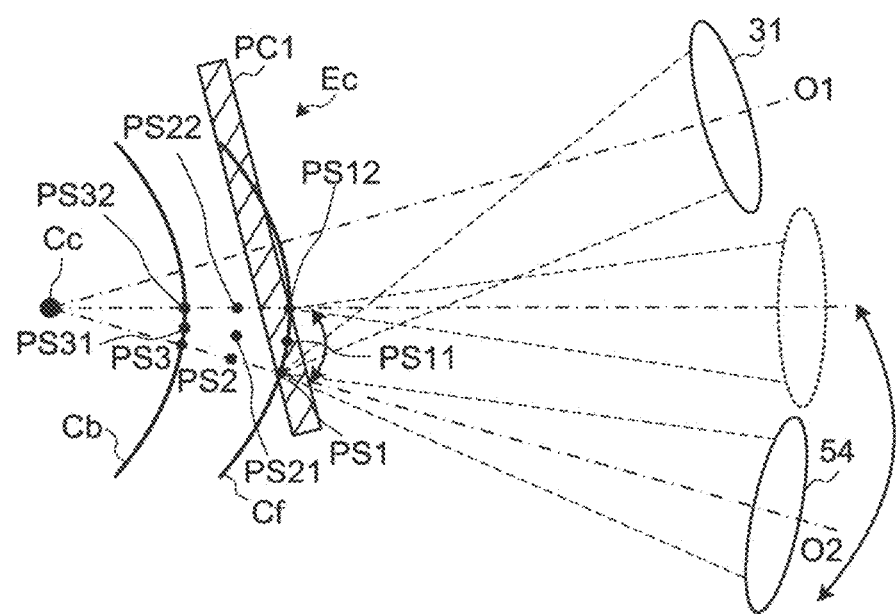
FIG. 6 is a schematic diagram for describing an example of the operation of the ophthalmic system according to the exemplary embodiment.

The control system of the slit lamp microscope 1 will be described with referring to FIG. 4 to FIG. 6. FIG. 4 shows an example of the configuration of the control system of the slit lamp microscope 1. Note that the computer 100 may include at least part of a plurality of elements constituting the control system.

<Controller 101>

The controller 101 controls each part of the slit lamp microscope 1. The controller 101 controls the observation-photographing system 6, the illumination system 8, the display device 130, the communication device 170, etc.

The controls for the observation-photographing system 6 may include any one or more of the followings: control for the variable magnification optical system 32; control for the image sensor 43; control for the focus mechanism 40; control for the movement mechanism 60 that moves the observation-photographing system 6; control for the focal position detector 150; and control for the scan position detector 160. The control for the variable magnification optical system 32 may include the control to change the magnification (magnification ratio) of an observation image or a photographed image of the subject's eye E in accordance with the content of an operation performed using the magnification operation knob 11. The control for the image sensor 43 may include any of the followings: the control to change the electric charge accumulation time, the sensitivity, the frame rate, etc. of the image sensor 43; and the control to send the image signal GS generated by the image sensor 43 to the image composition device 120. The control for the focus mechanism 40 may include the control to change the focal position of the observation-photographing system 6. The movement mechanism 60 may include, for example, the movement mechanism part 3, the support arms 16 and 17, and a mechanism that moves the support arms 16 and 17. The control for the movement mechanism 60 may include the control to rotate the observation-photographing system 6. The control for the focal position detector 150 may include the control to acquire the position detected by the focal position detector 150 and send the acquired position to the image composition device 120. The control for the scan position detector 160 may include the control to acquire the position detected by the scan position detector 160 and send the acquired position to the image composition device 120.

The controls for the illumination system 8 may include the followings: control for the illumination light source 51; control for the slit forming part 53; control for the focus mechanism 50; control for the movement mechanism 60 for moving the illumination system 8; control for the focal position detector 150; and control for the scan position detector 160. The control for the illumination light source 51 may include the control to switch on and off the illumination light source 51, and the control to change the quantity of the illumination light. The control for the slit forming part 53 may include the control to change the slit width, the control to translate the slit, and the control to rotate the slit. The control for the focus mechanism 50 may include the control to change the focal position of the slit light (focal position of the illumination system 8). The control for movement mechanism 60 may include the control to move the illumination system 8. The control for the focal position detector 150 may include the control to acquire the position detected by the focal position detector 150 and send the acquired position to the image composition device 120. The control for the scan position detector 160 may include the control to acquire a position detected by the scan position detector 160 and send the acquired position to the image composition device 120.

The controller 101 includes the focus controller 101A, the scan controller 101B, and the storage device 102.

The focus controller 101A executes the control for the focal position of the observation-photographing system 6 and the control for the focal position of the illumination system 8.

The controls carried out by the focus controller 101A will be described with referring to FIG. 5. FIG. 5 schematically shows the focal positions of the observation-photographing system 6 and the illumination system 8 with respect to the cornea Ec of the subject's eye E. As described above, the reference symbol 31 indicates the objective lens of the observation-photographing system 6, and the reference symbol 54 indicates the objective lens of the illumination system 8. The reference symbol Cf indicates the front surface of the cornea Ec, and the reference symbol Cb indicates the back surface of the cornea Ec. The reference symbol Cc indicates the position of the center of curvature of the cornea Ec (the position of the center of curvature of the front surface C0. For example, the rotation axis of the observation-photographing system 6 and that of the illumination system 8 both substantially coincide with the curvature center position Cc.

The focus controller 101A controls a scan in the depth direction with respect to the site of interest of the subject's eye E. The depth direction with respect to the site of interest corresponds to the radial direction in the rotational operation. Such a scan is called an r-scan. The focus controller 101A can execute the control of the focus mechanism 40 and the control of the focus mechanism 50 in an interlocking manner. For example, the focus controller 101A controls the focus mechanism 40 and the focus mechanism 50 to change the focal position of the observation-photographing system 6 and the focal position of the illumination system 8 in the order of the positions PS1, PS2 and PS3. The positions PS1, PS2 and PS3 are arranged along the depth direction of the site of interest, that is, along the depth direction in the subject's eye E. The observation-photographing system 6 can perform photography of the subject's eye E with depths of field respectively corresponding to the focal positions applied. For example, the observation-photographing system 6 can capture an image of the subject's eye E in the depth of field PC1 corresponding to the position PS1.

The focus controller 101A can execute the control for the imaging device 13 to capture an image and the interlocking control described above in an alternate manner. With this, the focus controller 101A can control the acquisition of a plurality of cross sectional images arranged in the depth direction of the site of interest of the subject's eye E. For example, the focus controller 101A can perform the control in such a way that an image of a cross section including the position PS1, an image of a cross section including the position PS2, and an image of a cross section including the position PS3 are sequentially captured.

The scan controller 101B performs control to move the scan position with respect to the site of interest of the subject's eye E in the horizontal direction (i.e., in the direction substantially orthogonal to the depth direction). Although detailed description is omitted, control to move the scan position in the vertical direction can also be executed in the same manner. Here, the vertical direction is substantially orthogonal to both the horizontal direction and the depth direction The operation of the scan controller 101B will be described with referring to FIG. 6. FIG. 6 schematically shows the focal positions of the observation-photographing system 6 and the illumination system 8 with respect to the cornea Ec. In FIG. 6, parts, sites, elements, etc. similar to those in FIG. 5 are indicated by the same reference symbols, and descriptions thereof are omitted unless otherwise stated.

The scan controller 101B controls a scan in the horizontal direction with respect to the site of interest of the subject's eye E. The horizontal direction with respect to the site of interest corresponds to the angle direction in the rotational operation. Such a scan is called a θ-scan. The scan controller 101B can execute the control of the movement mechanism 60 so as to interlock the rotation of the illumination system 8 and the rotation of the observation-photographing system 6 with each other. For example, the scan controller 101B moves the observation-photographing system 6 and the illumination system 8 in the order of the scan positions PS1, PS11, and PS12 in the horizontal direction.

The scan controller 101B can execute the control for the imaging device 13 to capture an image and the control for the movement mechanism 60 in an alternate manner. With this, the scan controller 101B can control the acquisition of a plurality of cross sectional images arranged in the horizontal direction in the site of interest of the subject's eye E. For example, the scan controller 101B can perform control in such a way that an image of a cross section including the position PS1, an image of a cross section including the position PS11, and an image of a cross section including the position PS12 are sequentially captured.

At each of the positions PS1, PS11, and PS12 in the horizontal direction, the focus controller 101A can change the focal position of the observation-photographing system 6 and the focal position of the illumination system 8 in the depth direction. As a result of this, one or more cross sectional image can be acquired for each of the positions PS1, PS2, PS3, P511, PS21, PS31, PS12, PS22, and PS32.

The storage device 102 stores various kinds of computer programs and data. The computer programs include an arithmetic program and a control program for operating the slit lamp microscope 1 according to a predetermined operation mode. The data includes various kinds of data used in various kinds of examinations. Scan information is an example of such data. For example, the scan information includes the followings: control information for moving the observation-photographing system 6 and the illumination system 8 to a plurality of scan positions of the site of interest; and control information for changing the focal position of the observation-photographing system 6 and that of the illumination system 8 to one or more positions in the depth direction corresponding to scan positions. These pieces of control information are stored in the storage device 102 in advance. By using the computer programs and the scan information stored in the storage device 102, the controller 101 can perform the control of the scan controller 101B to move the scan position in the horizontal direction and the control of the focus controller 101A to move the focal position, in an individual manner or in an interlocking manner.

The controller 101 includes a processor, a random access memory (RAM), a read only memory (ROM), a hard disk drive, etc. Control programs are stored in advance in a storage such as the ROM and the hard disk drive. The operation of the controller 101 is implemented through cooperation of software such as the control programs and hardware such as the processor. The controller 101 is disposed in the main body of the slit lamp microscope 1 (e.g., inside the base 4) or in the computer 100.

<Image Composition Device 120>

The image composition device 120 composes a plurality of cross sectional images acquired by the imaging device 13 according to the above-described control executed by the focus controller 101A and/or the scan controller 101B.

For example, the image composition device 120 composes a plurality of cross sectional images acquired by the imaging device 13 in parallel with performing the change in the focal position by the focus mechanism 40 and the focus mechanism 50. In this case, the plurality of cross sectional images is arranged in the depth direction. In other words, a plurality of cross sections corresponding to the plurality of cross sectional images is lain in the same plane. A composite image constructed from such a plurality of cross sectional images is a two dimensional cross sectional image with a depth of field that is deeper than those of individual cross sectional images. In other words, such a composite image is a pan-focus (or deep focus) two dimensional cross sectional image.

The image composition device 120 can compose a plurality of (two dimensional) cross sectional images whose cross sections are not lain in the same plane to construct a three dimensional image. Note that a three dimensional image refers to an image (image data) in which the positions of pixels are defined by a three dimensional coordinate system.

Stack data of a plurality of cross sectional images is an example of three dimensional images. The stack data is image data constructed by arranging a plurality of cross sectional images obtained at a plurality of differing scan positions in a three dimensional manner, based on the positional relationship of the scan positions. More specifically, the stack data is image data constructed by representing a plurality of cross sectional images, which are originally defined by individual two dimensional coordinate systems, by a single three dimensional coordinate system. That is, the stack data is image data constructed by embedding a plurality of cross sectional images in a single three dimensional space.

Volume data is another example of three dimensional images. The volume data is also referred to as voxel data. The volume data is image data in which voxels, which are three dimensional picture elements, are arranged in a three dimensional manner. The volume data is constructed, for example, by applying interpolation to stack data and three-dimensionalize (or voxelize) the pixels of the stack data interpolated.

In order to execute the image composition processing described above, the image composition device 120 includes the arrangement processor 121 and the composition processor 122.

The arrangement processor 121 determines an arrangement of a plurality of cross sectional images acquired by the aforementioned r-scan, θ-scan, or a combination of r-scan and θ-scan, based on a plurality of pieces of position information (e.g., focal positions, cross sectional positions) associated with the plurality of cross sectional images. The arrangement processor 121 then places the plurality of cross sectional images in accordance with the arrangement determined.

For example, the arrangement processor 121 receives focal positions of the slit light detected by the focal position detector 150 (e.g., the position information described above) from the controller 101, and then places the plurality of cross sectional images according to the focal positions received. As another example, the arrangement processor 121 receives, from the controller 101, rotational positions of the observation-photographing system 6 and the illumination system 8 detected by the scan position detector 160 (e.g., the position information described above), and then places the plurality of cross sectional images according the rotational positions received.

The composition processor 122 composes the plurality of cross sectional images arranged by the arrangement processor 121. This image composition process may include, for example, a process of constructing stack data, and may further include a process of constructing volume data.

By executing a series of processes described above, the image composition device 120 can construct a three dimensional image or a two dimensional image from a plurality of cross sectional images of the subject's eye E.

In another example, the image composition device 120 can compose a plurality of cross sectional images without using the position information described above. For example, the image composition device 120 may be configured to execute the following processes: applying image analysis to a plurality of cross sectional images to determine two or more image regions, all of which correspond to the same site in the subject's eye E, in two or more cross sectional images (the two or more image regions are called common regions); composing (or pasting together) the two or more cross sectional images in such a manner that the common regions overlap with each other. In the case where the image analysis described above is applied, the focal position detector 150 and the scan position detector 160 are not required. On the other hand, the image composition device 120 may be configured to perform adjustment of the positions (registration) of images with information obtained by the focal position detector 150 and/or the scan position detector 160, and then perform further registration with the image analysis.

An apparatus different from the slit lamp microscope 1 may have at least part of the functions of the image composition device 120. For example, a computer that is capable of communicating with the slit lamp microscope 1 may have at least part of the functions of the image composition device 120. As a specific example, a computer located in a facility where the slit lamp microscope 1 is installed (e.g., the computer terminal 3000-*n*, an intra-facility server) may have at least part of the functions of the image composition device 120. The management server 4000, or a computer that is capable of communicating with the management server 4000, may have at least part of the functions of the image composition device 120. The doctor's computer terminal 5000*m*, or a computer that is capable of communicating with the doctor's computer terminal 5000*m*, may have at least part of the functions of the image composition device 120.

<Focal Position Detector 150>

The focal position detector 150 includes, for example, the first focal position detector and the second focal position detector. The first focal position detector detects the focal position of the observation-photographing system 6, and the second focal position detector detects the focal position of the illumination system 8. The first focal position detector and/or the second focal position detector may include a position sensor such as an encoder or a potentiometer.

In another example, the first focal position detector may include a processor that determines the focal position of the observation-photographing system 6 based on the contents of controls executed by the focus controller 101A on the observation-photographing system 6. The contents of controls correspond to the history of controls.

Likewise, the second focal position detector may include a processor that determines the focal position of the illumination system 8 based on the contents of controls executed by the focus controller 101A on the illumination system 8 (i.e., the history of controls).

<Scan Position Detector 160>

The scan position detector 160 includes, for example, the first position detector and the second position detector. The first position detector detects the position of the observation-photographing system 6, and the second position detector detects the position of the illumination system 8. The first position detector and/or the second position detector includes, for example, a position sensor that detects the position of the base 4, and a rotation angle sensor that detects the positions of the support arms 16 and 17.

In another example, the first position detector may include a processor that determines the position of the observation-photographing system 6 based on the contents of controls (i.e., the history of controls) executed by the scan controller 101B on the observation-photographing system 6. Likewise, the second position detector may include a processor that determines the position of the illumination system 8 based on the contents of controls (i.e., the history of controls) executed by the scan controller 101B on the illumination system 8.

<Display Device 130>

The display device 130 displays various kinds of information under the control of the controller 101. For example, the display device 130 includes a flat panel display such as a liquid crystal display (LCD). The display device 130 may be provided in the main body of the slit lamp microscope 1 or may be provided in the computer 100.

<Operation Device 140>

The operation device 140 includes an operation device for operating the slit lamp microscope 1 and an input device for inputting information. The operation device 140 includes buttons and switches provided in the slit lamp microscope 1 (e.g., the operation handle 5 and the magnification operation knob 11), and operation devices provided in the computer 100 (e.g., a mouse and a keyboard). Further, the operation device 140 may include any kind of operation devices and any kind of input devices, such as a trackball, an operation panel, a switch, a button, and a dial.

The display device 130 and the operation device 140 are shown separately in FIG. 4. On the other hand, at least part of the display device 130 and at least part of the operation device 140 may be a single device. A touch screen is a specific example of such a single device.

<Communication Device 170>

The communication device 170 performs data communication between the slit lamp microscope 1 and another apparatus. The system of the data communication may be arbitrary. For example, the communication device 170 may include any one or more of a communication interface conforming to the Internet, a communication interface conforming to a dedicated line, a communication interface conforming to LAN, and a communication interface conforming to near field communication. The data communication may be either wireless communication or wired communication.

Data sent and received by the communication device 170 may be encrypted. If this is the case, for example, the controller 101 includes an encryptor and a decryptor. The encryptor is configured to encrypt data to be sent. The decryptor is configured to decrypts data having been received.

<Management Server 4000>

Figure 7:
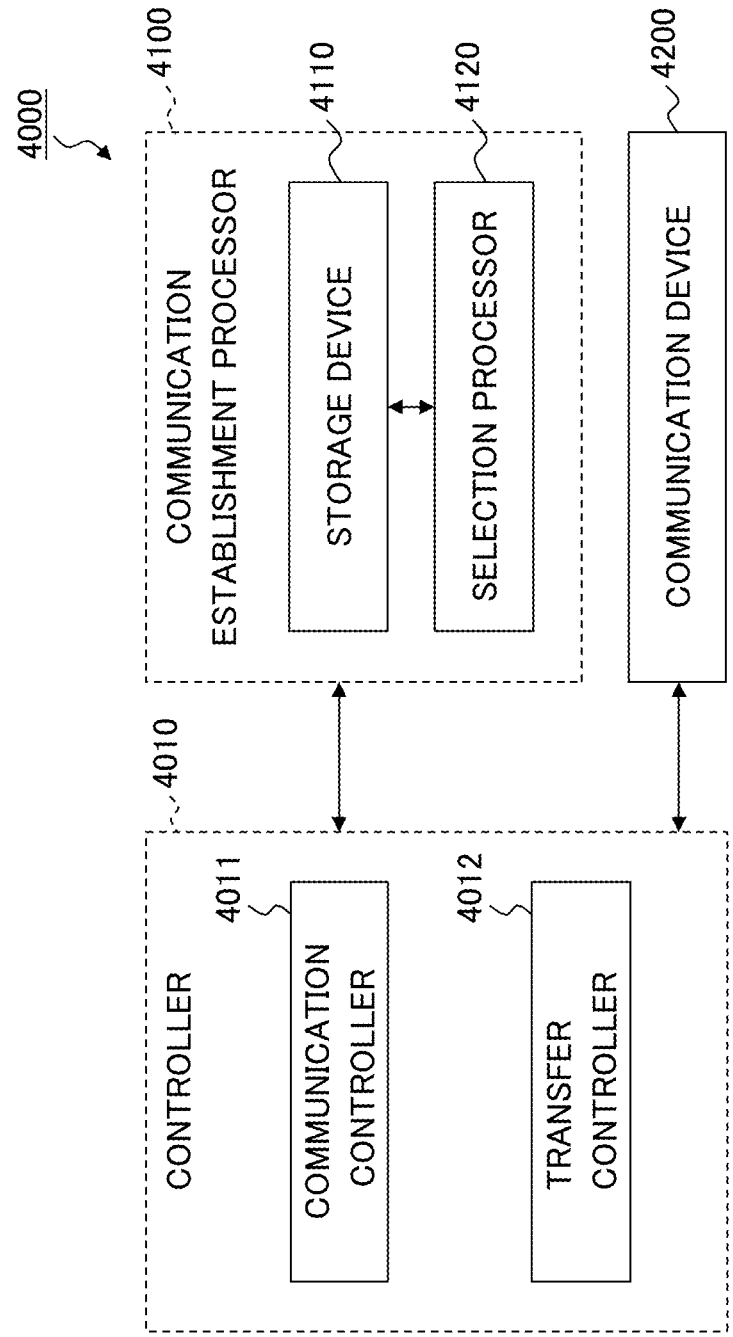
FIG. 7 is a schematic diagram illustrating an example of the configuration of the ophthalmic system according to the exemplary embodiment.

A description is given of the configuration of the management server 4000. The management server 4000 illustrated in FIG. 7 includes the controller 4010, the communication establishment processor 4100, and the communication device 4200.

<Controller 4010>

The controller 4010 executes control of each part of the management server 4000. The controller 4010 may be capable of executing other processing such as arithmetic processing. The controller 4010 includes a processor. The controller 4010 may further include a RAM, a ROM, a hard disk drive, a solid state drive, etc.

The controller 4010 includes the communication controller 4011 and the transfer controller 4012.

The communication controller 4011 performs control relating to the establishment of communication between a plurality of apparatuses that includes a plurality of ophthalmic imaging apparatus 2000-*i*$_n$, a plurality of computer terminals 3000-*n*, and a plurality of doctor's computer terminals 5000*m*. For example, the communication controller 4011 sends a control signal for establishing communication to each of two or more apparatuses selected by the selection processor 4120 from among a plurality of apparatuses included in the ophthalmic system 1000. The selection processor 4120 will be described later.

The transfer controller 4012 performs control relating to the exchange of information between two or more apparatuses whose communication has been established by the communication establishment processor 4100 (and the communication controller 4011). For example, the transfer controller 4012 functions to transfer information transmitted from one of the at least two apparatuses whose communication has been established by the communication establishment processor 4100 (and the communication controller 4011), to another apparatus.

As a specific example, in the case where the communication between the ophthalmic imaging apparatus 2000-*i*$_n$ and the doctor's computer terminal 5000*m* has been established, the transfer controller 4012 can transfer information transmitted from the ophthalmic imaging apparatus 2000-$i_n$ to the doctor's computer terminal 5000$m$. The information transmitted from the ophthalmic imaging apparatus 2000-$i_n$ may include an image acquired by the ophthalmic imaging apparatus 2000-$i_n$, information input to the ophthalmic imaging apparatus 2000-$i_n$, or the like. Conversely, the transfer controller 4012 can transfer information transmitted from the doctor's computer terminal 5000$m$ to the ophthalmic imaging apparatus 2000-$i_n$. The information transmitted from the doctor's computer terminal 5000$m$ may include the result of the selection of operation mode of the ophthalmic imaging apparatus 2000-$i_n$.

The transfer controller 4012 may have a function of processing information received from another apparatus. If this is the case, the transfer controller 4012 can transmit at least one of the received information and information created with the processing function, to an apparatus that is a destination of transfer.

For example, the transfer controller 4012 can extract part of the information transmitted from an apparatus such as the ophthalmic imaging apparatus 2000-$i_n$, and transmit the extracted information to an apparatus such as the doctor's computer terminal 5000$m$. Further, the management server 4000 or another apparatus may be configured to analyze information transmitted from an apparatus such as the ophthalmic imaging apparatus 2000-$i_n$. The information to be analyzed is, for example, an image of the subject's eye E. The transfer controller 4012 can send the result of the analysis of the information (and the original information) to an apparatus such as the doctor's computer terminal 5000$m$.

In the case where a plurality of cross sectional images has been transmitted from the slit lamp microscope 1 (the ophthalmic imaging apparatus 2000-$i_n$), the management server 4000 or another apparatus can construct a three dimensional image (e.g., stack data or volume data) from the plurality of cross sectional images, and the transfer controller 4012 can send the constructed three dimensional image to the doctor's computer terminal 5000$m$.

In the case where stack data has been transmitted from the slit lamp microscope 1 (the ophthalmic imaging apparatus 2000-$i_n$), the management server 4000 or another apparatus can construct volume data from the stack data, and the transfer controller 4012 can send the constructed volume data to the doctor's computer terminal 5000$m$.

The data processing executable by the management server 4000 or another apparatus is not limited to the examples described above and may include data processing of any kind.

<Communication Establishment Processor 4100>

The communication establishment processor 4100 performs processing to establish communication between at least two apparatuses selected from among a plurality of apparatuses including a plurality of ophthalmic imaging apparatus 2000-$i_n$, a plurality of computer terminals 3000-$n$ and a plurality of doctor's computer terminals 5000$m$. In the present embodiment, "establishing communication" refers to a concept which includes, for example, at least one of the followings: (1) establishing unidirectional communication from a state in which communication is disconnected; (2) establishing bidirectional communication from a state in which communication is disconnected; (3) switching from a state in which only data reception is possible to a state in which both data reception and data transmission are possible; and (4) switching from a state in which only data transmission is possible to a state in which both data transmission and data reception are possible.

In addition, the communication establishment processor 4100 can perform processing of disconnecting the established communication. In the present embodiment, "disconnecting communication" refers to a concept which includes, for example, at least one of the followings: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which data transmission and data reception are possible to a state in which only data reception is possible; and (5) switching from a state in which data transmission and data reception are possible to a state in which only data transmission is possible.

Each of the ophthalmic imaging apparatus 2000-$i_n$, the computer terminal 3000-$n$, and the doctor's computer terminal 5000$m$ can send at least one of the following communication requests to the management server 4000: a communication request (a call request) for calling another apparatus or the user thereof; and a communication request (an interruption request) for interrupting communication between two other apparatuses. A call request is issued manually or automatically, and an interrupt request is issued manually or automatically. The management server 4000 (the communication device 4200 therein) receives a communication request transmitted from the ophthalmic imaging apparatus 2000-$i_n$, the computer terminal 3000-$n$, or the doctor's computer terminal 5000$m$.

In the present embodiment, the communication establishment processor 4100 may include the selection processor 4120. For example, based on a communication request sent from the ophthalmic imaging apparatus 2000-$i_n$, the computer terminal 3000-$n$, or the doctor's computer terminal 5000$m$, the selection device 4120 selects one or more apparatuses other than the apparatus that has sent the communication request, from among the ophthalmic imaging apparatus 2000-$i_n$, the computer terminal 3000-$n$, and the doctor's computer terminal 5000$m$.

A specific example of the processing executed by the selection processor 4120 will be described. When a communication request sent from the ophthalmic imaging apparatus 2000-$i_n$ or the computer terminal 3000-$n$ is received (e.g., when a request for interpretation of an image acquired by the ophthalmic imaging apparatus 2000-$i_n$ is received), the selection processor 4120 selects, for example, any apparatus from among the plurality of doctor's computer terminals 5000$m$. The communication establishment processor 4100 establishes communication between the selected doctor's computer terminal 5000$m$, and at least one of the ophthalmic imaging apparatus 2000-$i_n$ and the computer terminal 3000-$n$.

The selection of an apparatus according to a communication request is performed, for example, based on a preset attribute. Examples of the attribute include types of examination (e.g., types of imaging modalities, types of images, types of diseases, types of candidate diseases), the degree of expertise required, the level of skill required, and types of languages. In order to realize the processing according to the present example, the communication establishment processor 4100 may include the storage 411 in which attribute information prepared in advance is stored. Attributes corresponding to the doctor's computer terminals 5000$m$ and/or attributes corresponding to the users thereof (doctors) are recorded in the attribute information.

The identification of doctors is carried out using, for example, doctor identifiers (doctor IDs) assigned in advance. Further, the identification of the doctor's computer terminals 5000$m$ is carried out using, for example, apparatus identifiers or network addresses. In a typical example, the attribute information includes attributes of each doctor such as the doctor's specialized field (e.g., the department, the specialized disease), the doctor's degree of expertise, the doctor's level of skill, or the types of languages the doctor is able to use.

When the selection processor 4120 refers to the attribute information, a communication request to be sent from the ophthalmic imaging apparatus 2000-$i_n$, the computer terminal 3000-$n$, or the doctor's computer terminal 5000$m$ may include information related to attributes. For example, an interpretation request (i.e., a diagnosis request) to be transmitted from the ophthalmic imaging apparatus 2000-$i_n$ may include any of the followings: (1) information indicating the type of imaging modality; (2) information indicating the type of image; (3) information indicating the name of disease or the name of candidate disease; (4) information indicating the degree of difficulty of interpretation; and (5) information indicating a language(s) the user of the ophthalmic imaging apparatus 2000-$i_n$ and/or the computer terminal 3000-$n$ uses.

When such an interpretation request is received, the selection processor 4120 can select one of the doctor's computer terminals 5000$m$ based on the interpretation request and the attribute information stored in the storage device 4110. In this selection processing, the selection processor 4120 checks the information related to the attributes included in the interpretation request against the information recorded in the attribute information stored in the storage device 4110. With this, the selection processor 4120 selects, for example, the doctor's computer terminal 5000$m$ corresponding to a doctor who satisfies any one of the following attributes: (1) a doctor who is specializing in the concerned imaging modality; (2) a doctor who is specializing in the concerned type of images; (3) a doctor who is specializing in the concerned disease (or the concerned candidate disease); (4) a doctor who is capable of perform interpretation of the concerned level of difficulty; and (5) a doctor who is capable of using the concerned language.

The correspondence between doctors and the doctor's computer terminals 5000$m$ is made by, for example, referring to doctor IDs input, at the time of logging in, to the doctor's computer terminals 5000$m$ (or to the ophthalmic system 1000).

<Communication Device 4200>

The communication device 4200 performs data communication with another apparatus. The another apparatus is, for example, any of the ophthalmic imaging apparatus 2000-$i_n$, the computer terminal 3000-$n$, and the doctor's computer terminal 5000$m$. The system of the data communication and encryption may be performed in the same manner as in the communication device 170 of the ophthalmic imaging apparatus 2000-$i_n$.

<Doctor's Computer Terminal 5000$m$>

Figure 8:
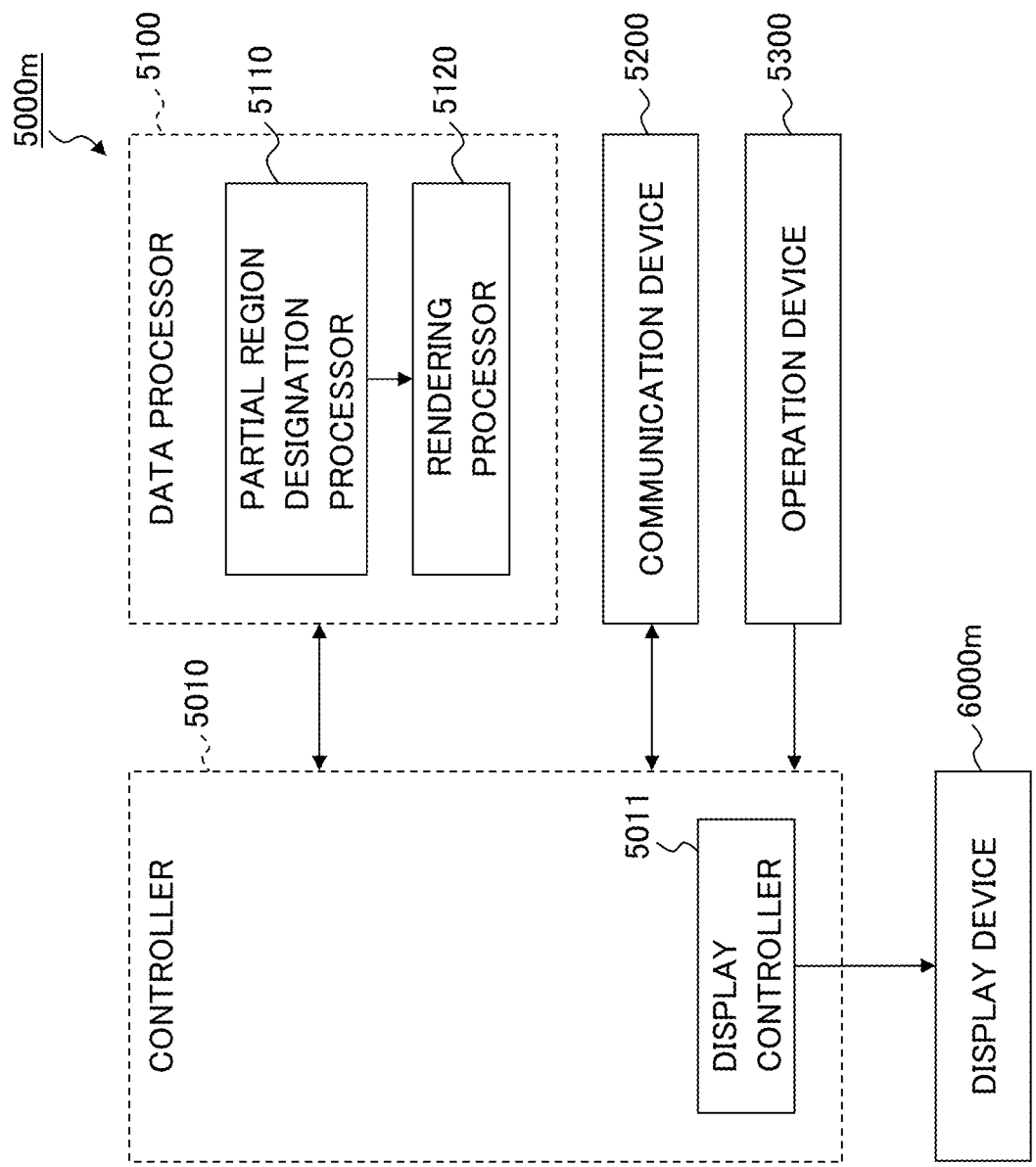
FIG. 8 is a schematic diagram illustrating an example of the configuration of the ophthalmic system according to the exemplary embodiment.

A description is given of the configuration of the doctor's computer terminal 5000$m$. The doctor's computer terminal 5000$m$ illustrated in FIG. 8 includes the controller 5010, the data processor 5100, the communication device 5200, and the operation device 5300.

<Controller 5010>

The controller 5010 executes control of each part of the doctor's computer terminal 5000$m$. The controller 5010 may be capable of executing other processing such as arithmetic processing. The controller 5010 includes a processor, a RAM, a ROM, a hard disk drive, a solid state drive, etc.

The controller 5010 includes the display controller 5011. The display controller 5011 controls the display device 6000$m$. The display device 6000$m$ may be included in the doctor's computer terminal 5000$m$ or may be a peripheral device connected to the doctor's computer terminal 5000$m$.

<Data Processor 5100>

The data processor 5100 executes various kinds of data processing.

For example, the data processor 5100 may be configured to construct a three dimensional image (e.g., stack data or volume data) from a plurality of cross sectional images sent from the slit lamp microscope 1 (the ophthalmic imaging apparatus 2000-$i_n$). Further, the data processor 5100 may be configured to construct volume data from stack data sent from the slit lamp microscope 1 (the ophthalmic imaging apparatus 2000-$i_n$).

The data processor 5100 includes the partial region designation processor 5110 and the rendering processor 5120.

The partial region designation processor 5110 designates a partial region of an image (image data) sent from the ophthalmic imaging apparatus 2000-$i_n$, or a partial region of an image displayed based on the sent image data.

A specific example of processing executable by the partial region designation processor 5110 will be described. When a plurality of cross sectional images of the subject's eye E has been acquired using the slit lamp microscope 1 (the ophthalmic imaging apparatus 2000-$i_n$), a three dimensional image of the subject's eye E is constructed by the slit lamp microscope 1, the management server 4000, the doctor's computer terminal 5000$m$, or another apparatus. Suppose that such a three dimensional image is input to the doctor's computer terminal 5000$m$. The controller 5010 stores the three dimensional image in the storage such as the hard disk drive described above.

The display controller 5011 can control the display device 6000$m$ to display an image based on the three dimensional image. For example, the controller 5010 sends the three dimensional image (e.g., stack data or volume data) to the rendering processor 5120. The rendering processor 5120 applies rendering to the three dimensional image to construct an image. The display controller 5011 controls the display device 6000$m$ to display the image constructed by the rendering processor 5120.

The user of the doctor's computer terminal 5000$m$ (doctor) can designate a partial region of the image displayed on the display device 6000$m$. The designation operation is performed using the operation device 5300. For example, the user can designate a desired area of the display image using a pointing device.

The partial region designation processor 5110 specifies a partial region of the three dimensional image corresponding to the partial region of the display image specified by the user. Here, the display image is an image obtained by rendering the three dimensional image. Therefore, the partial region of the three dimensional image corresponding to the partial region of the display image is easily specified based on the content of the rendering applied.

Another example will be explained. In the case where another image (referred to as a reference image) of the subject's eye E has been acquired in the past, it is possible to designate a partial region of the three dimensional image using the reference image. The reference image is, for example, an anterior segment image or an OCT image.

At least part of the reference image and at least part of the three dimensional image may depict the same site of the subject's eye E. Alternatively, a wide area image that depicts both the site depicted in at least part of the reference image and the site depicted in at least part of the three dimensional image can also be further utilized. By using such an image, the partial region designation processor 5110 can perform registration (position matching) between the reference image and the three dimensional image.

The display controller 5011 can control the display device 6000m to display the reference image (or the wide area image). The user can designate a partial region of the reference image (or a partial region of the wide area image) using the operation device 5300. The partial region designation processor 5110 can designate a partial region of the three dimensional image, based on the partial region of the reference image (or a partial region of the wide area image) designated by the user and a result of the registration between the reference image and the three dimensional image mentioned above.

Thus far, an example of the designation of a partial region of a three dimensional image by a user's operation has been described. However, methods of manual designation are not limited thereto. On the other hand, the partial region designation processor 5110 may be configured to perform automatic designation of a partial region of the three dimensional image, regardless of the user's operation. The automatic designation may be executed with an artificial intelligence processor (cognitive computing processor).

In one example, the partial region designation processor 5110 can designate a partial region of a three dimensional image by analyzing at least one of the three dimensional image and a display image based on the three dimensional image. For example, the partial region designation processor 5110 can specify an image region corresponding to a predetermined tissue of the subject's eye E by applying segmentation to the three dimensional image or to the display image, and designate a partial region based on the image region specified. The predetermined tissue of the subject's eye E is determined, for example, according to arbitrary conditions. Examples of the conditions include the types of imaging modalities, the types of images, and the disease names (the candidate disease names).

The rendering processor 5120 applies rendering to an image. For example, the rendering processor 5120 performs rendering on a three dimensional image, based on a partial region of the three dimensional image designated by the partial region designation processor 5110.

Methods of the rendering may be arbitrary. For example, the rendering may include three dimensional computer graphics. Three dimensional computer graphics is an arithmetic processing that creates an image having a stereoscopic effect by converting a virtual three dimensional object (e.g., a three dimensional image such as stack data or volume data) in a three dimensional space defined by a three dimensional coordinate system, into two dimensional information.

Examples of the rendering include the volume rendering method, the maximum intensity projection method (MIP), the minimum intensity projection method (MinIP), the surface rendering method, the multi planar reconstruction method (MPR), the projection image construction, and the shadowgram construction.

<Communication Device 5200>

The communication device 5200 performs data communication with another apparatus (e.g., any of the ophthalmic imaging apparatus $2000\text{-}i_n$, the computer terminal 3000-n, and the management server 4000). The system of the data communication and encryption may be performed in the same manner as in the communication device 170 of the ophthalmic imaging apparatus $2000\text{-}i_n$.

<Operation Device 5300>

The operation device 5300 includes an operation device for operating the doctor's computer terminal 5000m and an input device for inputting information. The operation device 5300 includes, for example, a mouse, a keyboard, a trackball, an operation panel, a switch, a button, a dial, or the like. The operation device 5300 may include a touch screen.

The operation device 5300 can be used to designate an operation mode of the slit lamp microscope 1. One or more operation modes are provided in advance for the slit lamp microscope 1. A three dimensional imaging mode can be provided in the present embodiment. The three dimensional imaging mode is an operation mode for acquiring three dimensional images of the subject's eye. In the three dimensional imaging mode, the controller 101 of the slit lamp microscope 1 controls the illumination system 8, the observation-photographing system 6, the movement mechanism 60, and the focus mechanisms 40 and 50 in an interlocking manner so that the imaging device 13 acquires a plurality of cross sectional images of the subject's eye E. Note that the operation modes of the slit lamp microscope 1 are not limited to the three dimensional imaging mode.

The device used for the designation of an operation mode is not limited to the operation device 5300. For example, the operation mode may be designated using the computer terminal 3000-n or the operation device 140 of the slit lamp microscope 1. The aspect of the operation mode designation is not limited to such manual designation. For example, an operation mode that applied to the concerned subject in the past can be obtained from an electronic medical record or the like and the operation mode applied in the past can be designated. In addition, it is possible to automatically designate an operation mode associated in advance with a specific disease. Further, an operation mode associated in advance with a specific type of examination (e.g., screening, health check, health examination, general examination, medical consultation) can be automatically designated.

<Usage Mode>

Figure 9:
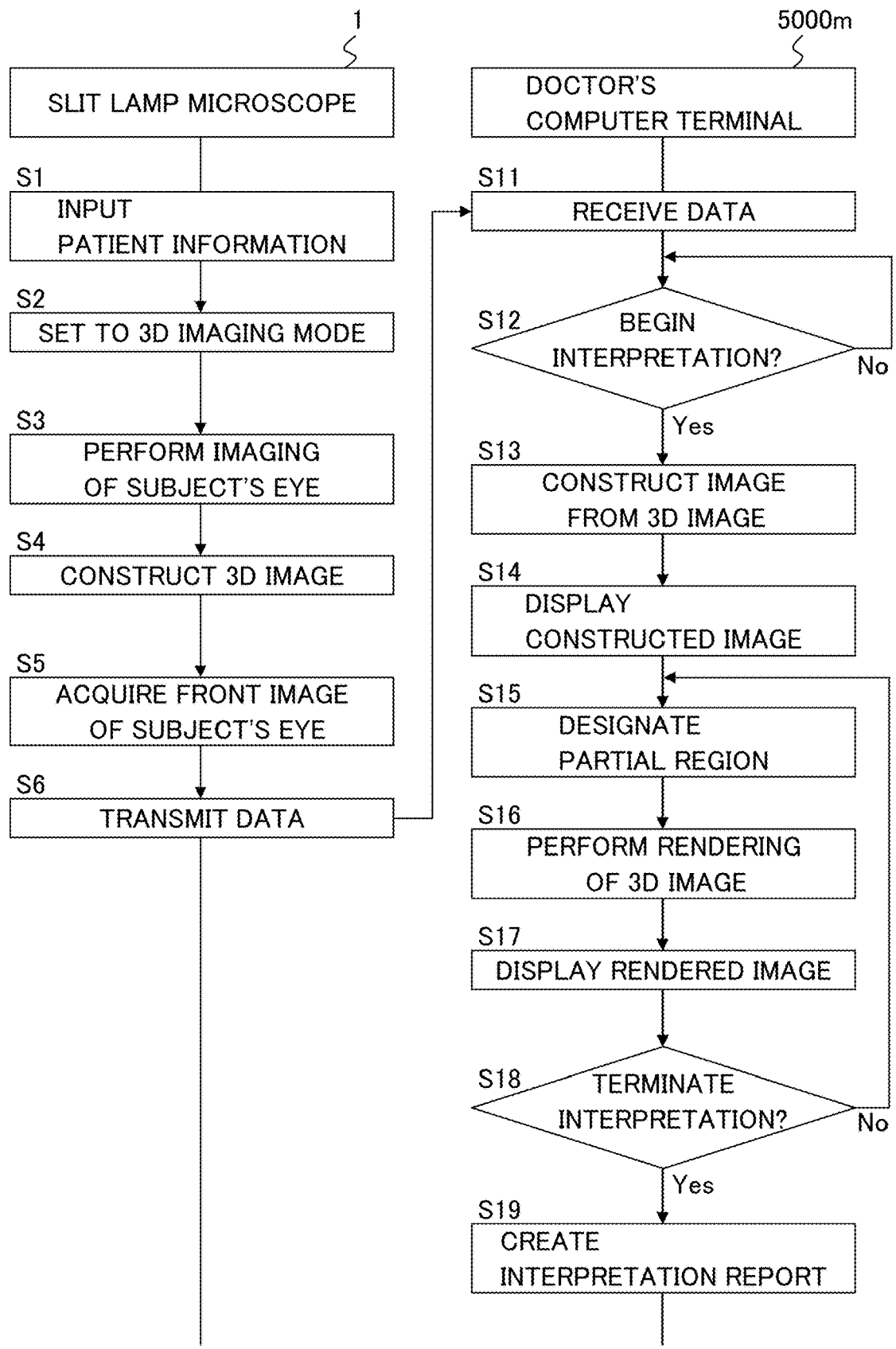
FIG. 9 is a sequence diagram illustrating an example of the usage mode of the ophthalmic system according to the exemplary embodiment.

The usage mode of the ophthalmic system 1000 according to the present embodiment will be described. FIG. 9 shows an example of the usage mode of the ophthalmic system 1000.

Suppose that the communication between the slit lamp microscope 1 (and/or the computer terminal 3000-n) and the doctor's computer terminal 5000m has already been established. Note that, as another example, the communication between the slit lamp microscope 1 (and/or the computer terminal 3000-n) and the doctor's computer terminal 5000m may be established at any timing during the period from the step S1 to step S6 described below.

(S1: Input Patient Information)

First, subject information is input to slit lamp microscope 1 (or to the computer terminal 3000-n). The subject information inputted is stored in the storage device 102. In the case where communication between the slit lamp microscope 1 (and/or the computer terminal 3000-n) and the doctor's computer terminal 5000m has already been established, the subject information inputted may be transmitted to the doctor's computer terminal 5000m (or to the management server 4000) at this stage. The subject information includes, for example, a subject identifier (subject ID) and background information.

The subject ID includes, for example, an identifier in a medical facility (a patient identifier), an identifier for a medical check, an identifier for a medical examination, or the like. These are examples only, and the kinds of the subject IDs are not limited to these exemplary IDs.

The background information is any kind of information related to the subject, and includes, for example, information about an arbitrary item recorded in the electronic medical record of the subject, an image stored in the subject's account, and the like. Typically, the background information includes the subject's data on items such as gender, age, height, weight, disease name, candidate disease name, examination result (e.g., visual acuity value, eye refractive power value, intraocular pressure value), an image (e.g., OCT image, fundus image, anterior segment image), examination history, and treatment history. These are examples only, and the kinds of the background information are not limited to these exemplary pieces of information (items, data).

For example, the user of the slit lamp microscope 1 (or the user of the computer terminal 3000-$n$) can input subject information using the operation device 140. In addition, the controller 101 and the communication device 170 can access an information system such as an electronic medical record system or a medical image archiving system via a communication path, to acquire subject information. In another example, subject information can be read out from a recording medium using a data reader. These are examples only, and the methods of inputting subject information are not limited to these exemplary methods.

(S2: Set to Three Dimensional Imaging Mode)

The operation mode of the slit lamp microscope 1 is set to the three dimensional imaging mode. As described above, the designation (or selection) of the operation mode is performed manually or automatically.

(S3: Perform Imaging of Subject's Eye)

The slit lamp microscope 1 performs the imaging of the subject's eye E with the three dimensional imaging mode that has been set in step S2. With this, a plurality of cross sectional images of the subject's eye E are acquired.

(S4: Construct Three Dimensional Image)

The image composition device 120 of the slit lamp microscope 1 constructs a three dimensional image, based on the plurality of cross sectional images acquired in step S2. As described above, the management server 4000, the doctor's computer terminal 5000$m$, or another apparatus may perform construction of the three dimensional image.

(S5: Acquire Front Image of Subject's Eye)

The slit lamp microscope 1 can acquire a front image of the subject's eye E. The timing of acquiring the front image is not limited to the timing described in this example. Note that the acquisition in this step is optional.

(S6: Transmit Data)

The controller 101 of the slit lamp microscope 1 controls the communication device 170 to transmit the acquired data to the doctor's computer terminal 5000$m$. The data to be transmitted includes at least the three dimensional image constructed in step S4 and may further include any one or both of the subject information input in step S1 and the front image acquired in step S5.

In the case where an apparatus other than the slit lamp microscope 1 executes the construction of the three dimensional image, the plurality of cross sectional images acquired in step S3 are transmitted.

The data transmitted from the slit lamp microscope 1 is transferred to the doctor's computer terminal 5000$m$ by the management server 4000.

(S11: Receive Data)

The communication device 5300 of the doctor's computer terminal 5000$m$ receives the data transmitted from the slit lamp microscope 1 in step S6. The controller 5010 stores the received data in the storage device described above.

(S12: Begin Interpretation?)

The doctor begins interpretation at a desired timing (S12: Yes).

(S13: Construct Image from Three Dimensional Image)

After the interpretation is started, the rendering processor 5120 constructs an image (a display image) automatically or in accordance with instructions issued from the user (the doctor).

(S14: Display Constructed Image)

The display controller 5011 controls the display device 6000$m$ to display the display image constructed in step S13. Note that the user can perform operations on the display image. For example, the doctor's computer terminal 5000$m$ can be configured in such a way that the orientation of the display image can be changed or the cross section represented by the display image can be changed.

(S15: Designate Partial Region)

The user designates a partial region of the display image using the operation device 5300. Here, the reference image and/or the wide area image described above may be used. In addition, designation of a partial region may be carried out in an automatic fashion.

(S16: Perform Rendering of Three Dimensional Image)

The rendering processor 5120 performs rendering of the three dimensional image based on the partial region designated in step S15. With this, a rendered image representing the partial region designated by the user can be acquired. That is, an image of the site of interest that the user is focusing on can be acquired.

(S17: Display Rendered Image)

The display controller 5011 controls the display device 6000$m$ to display the rendered image acquired in step S16.

The display controller 5011 can display position information indicating the position of the rendered image on the display device 6000. The position information may be, for example, information indicating the position and/or the area of the partial region designated in step S15, or information indicating the position and/or the area of the rendered image constructed in step S16. The position information may be displayed together with, for example, any one or more of the front image acquired in step S5, the reference image or wide area image described above, and a schema diagram of the eye. Typically, an image showing a position or an area in a schema diagrams or the above image can be displayed as position information.

(S18: Terminate Interpretation?)

The user can perform the interpretation while changing the site of interest as desired (S18: No). At that time, the user can refer to the subject information input in step S1 and the front image acquired in step S5.

(S19: Create Interpretation Report)

When the interpretation is completed (S18: Yes), the user fills in the interpretation report with information obtained by the interpretation and results of diagnosis. The interpretation report created is transmitted, for example, to the electronic medical chart system or the like and stored therein. The interpretation report may also be sent to the facility where the slit lamp microscope 1 is installed. This terminates the processing according to the present example.

Modification Example

A modification example of the present embodiment will be described.

The configuration for changing the focal positions of the slit lamp microscope 1 is not limited to the focus mechanisms 40 and 50 described above.

For example, it is possible to employ a slit lamp microscope that is configured to acquire two or more images of the subject's eye using two or more imaging devices (two or more anterior eye segment cameras), disclosed in Japanese Unexamined Patent Application Publication No. 2013-248376, and determine the focal positions (target positions) by analyzing the images acquired by the two or more imaging devices.

Another example of the configuration for changing the focal positions includes the followings. A slit lamp microscope of the present example includes an imaging device, a driver, and a focus controller. The imaging device photographs the subject's eye to acquire a right image and a left image. The driver drives the optical system, which includes the imaging device, at least in the direction along the working distance. Based on the right image and the left image output from the imaging device, the focus controller controls the driver to automatically perform the focusing operation on the subject's eye.

<Actions and Effects>

Some actions and effects exerted by the embodiment described above will be described.

The ophthalmic system (1000) according to the embodiment includes a slit lamp microscope (1, 2000-$i_n$) and an information processing apparatus (the doctor's computer terminal 5000*m*) connected to each other via a communication path (N).

The slit lamp microscope includes an image acquisition device (the observation-photographing system 6, the illumination system 8, the movement mechanism 60, etc.) and a first communication device (the communication device 170). The image acquisition device acquires a three dimensional image by photographing a subject's eye. The first communication device transmits the three dimensional image acquired, to the information processing apparatus.

The information processing apparatus includes a second communication device (5200), a display controller (5011), a partial region designation processor (5110), and a rendering processor (5120). The second communication device receives the three dimensional image transmitted by the first communication device. The display controller displays a first image based on the received three dimensional image on a display device (the display device 6000*m*). The partial region designation processor designates a partial region of the first image displayed. The rendering processor renders the three dimensional image based on the partial region designated, to construct a second image. The display controller displays the constructed second image on the display device.

According to the ophthalmic system of the present embodiment thus configured, a three dimensional image of the subject's eye can be acquired first with a slit lamp microscope, and then the acquired three dimensional image can be sent to the information processing apparatus. In addition, a doctor can carry out rendering of the three dimensional image as desired using the information processing apparatus. Therefore, the doctor can observe any desired site of interest of the subject's eye while performing the rendering, as one likes, of the three dimensional image acquired in advance by the slit lamp microscope.

As a result of this, it becomes unnecessary for a doctor to perform operations of a slit lamp microscope in real time from a remote location in order to acquire an image of a subject's eye. Moreover, there is also an advantage that a doctor can perform medical image interpretation, at a remote location, of an image acquired by a slit lamp microscope which is most widely and most frequently used for diagnostic imaging in the field of ophthalmology.

Therefore, according to the ophthalmic system of the present embodiment, an ophthalmic telemedicine technology capable of effectively utilizing a slit lamp microscope can be provided.

In the present embodiment, the information processing apparatus may further include an operation device (5300). Further, the partial region designation processor (5110) can designate a partial region based on a signal output from the operation device.

According to such a configuration, a doctor can designate a desired site of the subject's eye manually and observe a rendered image of the site designated.

In the present embodiment, the partial region designation processor may be configured to analyze at least one of the three dimensional image of the subject's eye and the first image, to designate a partial region of the first image.

According to such a configuration, the partial region can be automatically designated. As a result, the efficiency of interpretation work can be improved. Further, interpretation work can be supported and assisted using a computer.

In the present embodiment, the image acquisition device of the slit lamp microscope may include an illumination system (8), an imaging system (the observation-photographing system 6), and a movement device (the movement mechanism 60). The illumination system illuminates the subject's eye with slit light. The imaging system guides returning light of the slit light from the subject's eye to an imaging device (13). The movement device moves the illumination system and the imaging system. Furthermore, the ophthalmic system (1) of the present embodiment may include a three dimensional image construction processor. The three dimensional image construction processor constructs a three dimensional image from a plurality of cross sectional images acquired by the imaging device in parallel with movement of the illumination system and the imaging system. The three dimensional image construction processor corresponds to, for example, the image composition device 120 of the slit lamp microscope 1. Alternatively, the three dimensional image construction processor may be provided in the doctor's computer terminal 5000*m* (information processing apparatus) or another apparatus.

According to such a configuration, images of a plurality of cross sections (cross sectional images) of the subject's eye can be acquired in parallel with change in the illumination angle and change in the photographing angle with respect to the subject's eye, and a three dimensional image can be constructed from the cross sectional images acquired.

In the present embodiment, the image acquisition device of the slit lamp microscope may include a focal position changer. The focal position changer is configured to change at least one of the focal position of the illumination system and the focal position of the imaging system. In addition, the three dimensional image construction processor can construct a three dimensional image from a plurality of cross sectional images acquired by the imaging device in parallel with both movement of at least one of the illumination system and the imaging system and change in at least one of the focal position of the illumination system and the focal position of the imaging system.

With such a configuration, photography of the subject's eye can be performed multiple times in parallel with change in the focal positions with respect to the subject's eye, and a three dimensional image can be constructed from a plurality of cross sectional images acquired through the multiple times of photography.

In the present embodiment, the ophthalmic system may include an operation mode designation device for designating an operation mode of the slit lamp microscope. The operation mode designation device corresponds to, for example, the operation device 5300 of the doctor's computer terminal 5000m, the operation device 140 of the slit lamp microscope 1, the computer terminal 3000-n, or another apparatus. In addition, the slit lamp microscope may include a controller (101). The controller of the slit lamp microscope is configured to control the illumination system, the imaging system, the movement device, and the focal position changer in an interlocking manner to make the imaging device acquire a plurality of cross sectional images of the subject's eye when a three dimensional imaging mode has been designated by the operation mode designation device.

According to such a configuration, it is possible to automatically perform the acquisition of a plurality of cross sectional images for constructing a three dimensional image of the subject's eye.

In the present embodiment, the display controller (5011) may be configured to display position information, indicating a position of the second image constructed from the three dimensional image by the rendering processor, on the display device. The position information is displayed together with the first image or another image, for example.

With such a configuration, a doctor can easily grasp to which site of the subject's eye the second image corresponds. That is, the doctor can easily grasp to which portion of the three dimensional image the second image corresponds.

In the present embodiment, the slit lamp microscope may include a reception part that receives subject information. The reception part corresponds to, for example, the operation device 140, the communication device 170, or the like of the slit lamp microscope 1. Furthermore, the first communication device of the slit lamp microscope may be configured to transmit the subject information together with the three dimensional image of the subject's eye acquired by the image acquisition device.

With such a configuration, a doctor can conduct medical image interpretation and/or diagnosis with referring to the subject information together with the rendered image of the three dimensional image.

In the present embodiment, the image acquisition device of the slit lamp microscope may be configured to acquire a front image of the subject's eye by photographing the subject's eye. Furthermore, the first communication device of the slit lamp microscope may be configured to transmit the front image of the subject's eye together with the three dimensional image of the subject's eye acquired by the image acquisition device.

With such a configuration, a doctor can conduct medical image interpretation and/or diagnosis with referring to the front image together with the rendered image of the three dimensional image.

In the present embodiment, the doctor's computer terminal 5000m is an example of an ophthalmic information processing apparatus. The ophthalmic information processing apparatus (the doctor's computer terminal 5000m) includes a communication device (5300), a display controller (5011), a partial region designation processor (5110), and a rendering processor (5120). The communication device receives a three dimensional image acquired by photographing a subject's eye with a slit lamp microscope (1) via a communication path (N). The display controller displays a first image based on the received three dimensional image on a display device (the display device 6000m). The partial region designation processor designates a partial region of the first image displayed. The rendering processor renders the three dimensional image based on the partial region designated, to construct a second image. In addition, the display controller displays the constructed second image on the display device.

According to such an ophthalmic information processing apparatus, like the ophthalmic system of the present embodiment, it is possible to provide an ophthalmic telemedicine technology capable of effectively utilizing a slit lamp microscope.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic system comprising:
   a slit lamp microscope; and
   an information processing apparatus connected to the slit lamp microscope via a communication path;
   the slit lamp microscope includes
      an image acquisition device that acquires a three dimensional image by photographing a subject's eye, and
      a first communication device that transmits the three dimensional image to the information processing apparatus;
   the information processing apparatus includes
      a second communication device that receives the three dimensional image transmitted by the first communication device,
      a display controller that displays a first image based on the three dimensional image on a display device,
      a partial region designation processor that designates a partial region of the first image, and
      a rendering processor that renders the three dimensional image based on the partial region to construct a second image;
   the display controller displays the second image on the display device;
   the image acquisition device includes
      an illumination system that illuminates the subject's eye with slit light,
      an imaging system that guides returning light of the slit light from the subject's eye to an imaging device, and
      a movement device that moves at least one of the illumination system and the imaging system;
   the image acquisition device further includes a focal position changer for changing at least one of a focal position of the illumination system and a focal position of the imaging system; and
   the ophthalmic system further includes a three dimensional image construction processor that constructs a three dimensional image based on a plurality of cross sectional images acquired by the imaging device in parallel with both movement of the at least one of the illumination system and the imaging system and change in the at least one of the focal position of the illumination system and the focal position of the imaging system.

2. The ophthalmic system of claim 1, wherein
the information processing apparatus further comprises an operation device, and
the partial region designation processor designates the partial region based on a signal output from the operation device.

3. The ophthalmic system of claim 1, wherein the partial region designation processor analyzes at least one of the three dimensional image and the first image to designate the partial region.

4. The ophthalmic system of claim 1, further comprising an operation mode designation device for designating an operation mode of the slit lamp microscope, wherein
the slit lamp microscope further comprises a controller that controls the illumination system, the imaging system, the movement device, and the focal position changer in an interlocking manner to make the imaging device acquire the plurality of cross sectional images when a three dimensional imaging mode has been designated using the operation mode designation device.

5. The ophthalmic system of claim 1, wherein the display controller displays position information indicating a position of the second image on the display device.

6. The ophthalmic system of claim 1, wherein
the slit lamp microscope further comprises a reception part that receives subject information, and
the first communication device transmits the subject information together with the three dimensional image.

7. The ophthalmic system of claim 1, wherein
the image acquisition device further acquires a front image by photographing the subject's eye, and
the first communication device transmits the front image together with the three dimensional image.

8. An ophthalmic information processing apparatus comprising:
a communication device that receives, via a communication path, a three dimensional image acquired by photographing a subject's eye with a slit lamp microscope and an image acquisition device;
a display controller that displays a first image based on the three dimensional image on a display device;
a partial region designation processor that designates a partial region of the first image;
a rendering processor that renders the three dimensional image based on the partial region to construct a second image,
the display controller displays the second image on the display device
the image acquisition device includes
an illumination system that illuminates the subject's eye with slit light,
an imaging system that guides returning light of the slit light from the subject's eye to an imaging device, and
a movement device that moves at least one of the illumination system and the imaging system;
the image acquisition device further includes a focal position changer for changing at least one of a focal position of the illumination system and a focal position of the imaging system; and
the ophthalmic system further includes a three dimensional image construction processor that constructs a three dimensional image based on a plurality of cross sectional images acquired by the imaging device in parallel with both movement of the at least one of the illumination system and the imaging system and change in the at least one of the focal position of the illumination system and the focal position of the imaging system.

9. A method of processing ophthalmic information executed by an ophthalmic system comprising a slit lamp microscope and an information processing apparatus connected to the slit lamp microscope via a communication path, the method comprising:
acquiring a three dimensional image by photographing a subject's eye with the slit lamp microscope;
transmitting the three dimensional image from the slit lamp microscope to the information processing apparatus;
receiving the three dimensional image with the information processing apparatus;
displaying a first image based on the three dimensional image on a display device;
designating a partial region of the first image;
constructing a second image by rendering the three dimensional image based on the partial region;
displaying the second image on the display device;
illuminating the subject's eye with slit light by an illumination system;
guiding returning light of the slit light from the subject's eye to an imaging device having an imaging system;
moving at least one of the illumination system and the imaging system;
changing at least one of a focal position of the illumination system and a focal position of the imaging system; and
constructing a three dimensional image based on a plurality of cross sectional images acquired by the imaging device in parallel with both the moving of the at least one of the illumination system and the imaging system and the changing of the at least one of the focal position of the illumination system and the focal position of the imaging system.

10. A method of processing ophthalmic information executed by an information processing apparatus that is connected to a slit lamp microscope via a communication path, the method comprising:
receiving a three dimensional image acquired by photographing a subject's eye with the slit lamp microscope via a communication path;
displaying a first image based on the three dimensional image on a display device;
designating a partial region of the first image;
constructing a second image by rendering the three dimensional image based on the partial region;
displaying the second image on the display device;
illuminating the subject's eye with slit light by an illumination system;
guiding returning light of the slit light from the subject's eye to an imaging device having an imaging system;
moving at least one of the illumination system and the imaging system;
changing at least one of a focal position of the illumination system and a focal position of the imaging system; and
constructing a three dimensional image based on a plurality of cross sectional images acquired by the imaging device in parallel with both the moving of the at least one of the illumination system and the imaging system and the changing of the at least one of the focal position of the illumination system and the focal position of the imaging system.

11. The ophthalmic system of claim 1, wherein the illumination system and the imaging system are configured to move independently from one another.

12. The ophthalmic system of claim 1, further comprising:
a scan controller that controls the movement of at least one of the illumination system and the imaging system; and
a focus controller that changes at least one of the focal position of the illumination system and the focal position of the imaging system,
the movement control and focus changes performed by the scan controller and the focus controller being performed dependent upon each other in an interlocking manner to acquire the plurality of cross sectional images.

13. The ophthalmic system of claim 1, wherein each of the plurality of cross sectional images are assigned information regarding a cross section position, the focal position of the illumination system, and the focal position of the imaging system.

14. The ophthalmic system of claim 13, wherein the three dimensional image construction processor is further configured to construct the three dimensional image based on the information regarding the cross section position, the focal position of the illumination system, and the focal position of the imaging system assigned to each of the plurality of cross sectional images.

15. The ophthalmic system of claim 1, the focal position changer is configured to change the focal position of at least one of the illumination system and the imaging system by at least one of moving an objective lens along an optical axis, moving a focusing lens along the optical axis, and moving at least one of the illumination system and the imaging system.

* * * * *